US006882883B2

(12) United States Patent
Condie et al.

(10) Patent No.: US 6,882,883 B2
(45) Date of Patent: Apr. 19, 2005

(54) IMPLANTABLE MEDICAL DEVICE (IMD) SYSTEM CONFIGURABLE TO SUBJECT A PATIENT TO A STRESS TEST AND TO DETECT MYOCARDIAL ISCHEMIA WITHIN THE PATIENT

(75) Inventors: Catherine R. Condie, Shoreview, MN (US); Robert W. Stadler, Shoreview, MN (US); Lee Stylos, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 396 days.

(21) Appl. No.: 09/945,195

(22) Filed: Aug. 31, 2001

(65) Prior Publication Data

US 2003/0045908 A1 Mar. 6, 2003

(51) Int. Cl.⁷ .............................................. A61N 1/362
(52) U.S. Cl. ........................................................ 607/11
(58) Field of Search ............................ 607/4, 5, 11, 30, 607/32; 600/510, 515, 516, 517, 518

(56) References Cited

U.S. PATENT DOCUMENTS

| | | | |
|---|---|---|---|
| 4,933,873 A | * 6/1990 | Kaufman et al. | 704/270 |
| 5,010,888 A | 4/1991 | Jadvar et al. | 128/696 |
| 5,081,987 A | * 1/1992 | Nigam | 607/19 |
| 5,135,004 A | * 8/1992 | Adams et al. | 600/508 |
| 5,271,395 A | 12/1993 | Wahlstrand et al. | 607/9 |
| 5,464,432 A | * 11/1995 | Infinger et al. | 607/5 |
| 5,662,688 A | * 9/1997 | Haefner et al. | 607/5 |
| 5,836,975 A | 11/1998 | DeGroot | 607/5 |
| 6,128,526 A | 10/2000 | Stadler et al. | 600/517 |
| 6,190,324 B1 | * 2/2001 | Kieval et al. | 600/483 |
| 6,249,703 B1 | * 6/2001 | Stanton et al. | 607/30 |
| 6,285,898 B1 | * 9/2001 | Ben-Haim | 600/374 |
| 6,351,670 B1 | * 2/2002 | Kroll | 607/5 |

OTHER PUBLICATIONS

Atar, S. et al., "Transthoracic Stress Echocardiography With Transesophageal Atrial Pacing for Bedside Evaluation of Inducible Myocardial Ischemia in Patients With New–Onset Chest Pain," Am. J. Cardiol., vol. 86, p. 12–16, Jul. 1, 2000.

* cited by examiner

Primary Examiner—Jeffrey R. Jastrzab
(74) Attorney, Agent, or Firm—Paul H. McDowall; Girma Wolde-Michael

(57) ABSTRACT

Various implantable medical devices (IMDs) are disclosed for implantation in a patient. The IMD includes pacing circuitry configured to selectively produce pacing pulses at a programmable pacing rate. In one embodiment, the IMD is configurable to subject a patient to a stress test. The IMD may be configurable to subject the patient to the stress test at the time specified by stored timing information, or in response to a signal (e.g., from a patient activator). Another embodiment of the implantable medical device (IMD) includes sensor circuitry, a memory for storing data, and a control unit. The sensor circuitry produces sensor data relating to cardiac condition. The control unit is configurable to store the sensor data in the memory until a trigger signal is received. Methods are described for performing a stress test in a patient with an IMD, and for subsequently reproducing cardiac operational states.

41 Claims, 21 Drawing Sheets

IMPLANTABLE MEDICAL DEVICE (IMD) SYSTEM CONFIGURABLE TO SUBJECT A PATIENT TO A STRESS TEST AND TO DETECT MYOCARDIAL ISCHEMIA WITHIN THE PATIENT

BACKGROUND OF THE INVENTION

1. Field of the Invention

This invention relates generally to implantable medical device systems, and, more particularly, to implantable medical device systems including implantable medical devices for providing cardiac arrhythmia therapies to patients having the devices implanted within.

2. Description of the Related Art

Myocardial or cardiac ischemia is an intermediate condition in coronary artery disease during which the heart tissue is slowly or suddenly starved of oxygen and other nutrients. Myocardial ischemia is usually caused by blockage of a coronary artery, usually due to atherosclerotic plaque. Myocardial ischemia may also be caused by blood clots (which tend to form on plaque), artery spasms or contractions, or any of the above conditions in combination. If adequate blood flow to affected heart tissue is not restored, the affected heart tissue will die. When blood flow is completely blocked to the heart, myocardial ischemia can lead to myocardial infarction (i.e., a heart attack).

Myocardial ischemia can be symptomatic or silent. Symptomatic myocardial ischemia is characterized by chest pain (i.e., "angina pectoris" or simply "angina"), especially during physical exertion. People with angina are at risk of having a heart attack. Those suffering silent myocardial ischemia have no signs, and are typically at greater risk of having a heart attack with no warning than those with symptomatic myocardial ischemia.

Non-invasive tests used to diagnose myocardial ischemia and other types of heart disease include resting electrocardiogram (ECG), ambulatory ECG (i.e., Holter monitoring), exercise stress test (i.e., exercise ECG), and echocardiography. Invasive diagnostic tests requiring intravenous injection include pharmacological stress tests and nuclear imaging techniques. Other invasive imaging techniques include transesophageal echocardiography and coronary angiography (i.e., cardiac catheterization).

In an exercise stress test, a patient walks on a treadmill, or pedals an exercise bicycle, at increasingly higher levels of physical exertion. The patient's heart rate and blood pressure increase with the levels of physical exertion. In a pharmacological stress test, a drug (e.g., dipyridamole, dobutamine, adenosine, etc.) is administered intravenously to increase heart rate and blood pressure in a manner similar to the effects of physical exertion. During exercise and pharmacological stress tests, the patient's heart rate and blood pressure are monitored. If the patient's heart tissue does not receive needed amounts of oxygen and nutrients, the patient experiences myocardial ischemia.

Non-invasive and free of chemical side effects, exercise stress tests are typically preferred over pharmacological stress tests. Invasive pharmacological stress tests are usually performed on patients that cannot tolerate exercise stress tests (e.g., patients with physical limitations such as back trouble, joint disease, marked fatigue, etc.).

Exercise stress tests are, however, often difficult and costly to perform. For example, an exercise stress test requires special equipment, several technicians, and patient training. Stress tests typically have a target heart rate which is usually determined using the formula $0.85 \cdot (220\text{-age})$. To undergo an exercise stress test, a patient must be both willing and able to physically exert themselves to the target heart rate. Many patients have a difficult time reaching the target heart rate, especially in pharmacological stress tests.

Transesophageal atrial pacing has also been used to elevate heart rates and test for myocardial ischemia. Transesophageal atrial pacing takes advantage of the anatomical proximity of the esophagus to the left atrium of the heart for minimally invasive heart stimulation. In preparation for transesophageal atrial pacing, a patient swallows an electrode connected to one end of a lead. While in the esophagus, the electrode is positioned near the left atrium of the patient's heart by adjusting the lead length. A stimulator is coupled to the other end of the lead, and produces electrical pulses which electrically stimulate (i.e., "pace") the left atrium of the heart. In addition to providing a method for temporary atrial pacing in patients whose heart rates are too slow or irregular to meet the demands of their bodies (i.e., patients with bradycardia), transesophageal pacing also offers an alternative method for elevating heart rates for diagnosis of myocardial ischemia and other types of heart disease.

The present invention is directed to a system and method facilitating noninvasive testing for myocardial ischemia in patients with an implantable medical device (e.g., an implantable pulse generator or IPG, an implantable cardioverter defibrillator or ICD, etc.). The system and method may eliminate the need for invasive tests for myocardial ischemia in such patients.

SUMMARY OF THE INVENTION

Several different embodiments of an implantable medical device (IMD) are disclosed for implantation in a patient. The IMD includes pacing circuitry configured to selectively produce pacing pulses at a programmable pacing rate for delivery to muscle tissue of a heart (i.e., myocardium) of the patient. In one embodiment, the IMD is configurable to subject the patient to a stress test. During the stress test, the pacing rate is increased from a start rate to a stop rate, wherein the stop rate is greater than the start rate, and stress test data is acquired and stored within the IMD. The IMD may be configurable to store timing information specifying a time the IMD is to subject the patient to the stress test, and to subject the patient to the stress test at the time specified by the timing information. Alternately, the IMD may be configurable to subject the patient to the stress test in response to a signal (e.g., a radio frequency signal generated by a patient activator when the patient activates a pushbutton of the patient activator). The IMD may also be configurable to provide the stress test data stored within the IMD.

The implantable medical device (IMD) may be configurable to detect one or more signs of myocardial ischemia within the patient during the stress test, and to abort the stress test when the one or more signs are detected. The one or more signs of myocardial ischemia may include, for example, deviation of an ST segment of an electrogram (EGM) waveform from an isoelectric baseline of the electrogram (EGM) waveform. Alternately, or in addition, the IMD may abort a stress test in progress at a time a signal is received (e.g., a radio frequency signal generated by a patient activator when the patient activates a pushbutton of the patient activator).

A system is described including a programming unit and the implantable medical device (IMD) described above. The programming unit is configured to produce a first signal (e.g., a radio frequency signal), and the IMD is adapted to receive the first signal and configured to subject the patient to a stress test dependent upon the first signal. The first signal may, for example, convey timing information specifying a time the IMD is to subject the patient to the stress test.

The system may also include a patient activator configured to produce a second signal in response to input from the patient (e.g., a radio frequency signal generated by the patient activator when the patient activates a pushbutton of the patient activator). The implantable medical device (IMD) may be configurable to respond to the second signal by subjecting the patient to the stress test. Alternately, or in addition, the IMD may be configurable to respond to the second signal by aborting a stress test in progress at a time the second signal is received.

Another embodiment of the implantable medical device (IMD) includes sensor circuitry, a memory for storing data, and a control unit coupled to the pacing circuitry, the sensor circuitry, and the memory. The sensor circuitry is configured to receive a signal from at least one sensor (e.g., an electrode) and to produce sensor data dependent upon the sensor signal, wherein the sensor data includes data indicative of an operational state of the patient's heart. The control unit is configurable to store the sensor data in the memory until a trigger signal is received. The trigger signal may be generated when the patient suffers from one or more signs of myocardial ischemia. The control unit may also be configurable to use the sensor data stored in the memory to reproduce the operational state of the patient's heart.

The control unit may be configurable to analyze the sensor data to detect the one or more signs of myocardial ischemia within the patient, and to generate the trigger signal when the one or more signs of myocardial ischemia are detected within the patient. Alternately, or in addition, the IMD may also include a telemetry unit coupled to the control unit and configured to send and receive signals, wherein the trigger signal is received via the telemetry unit. For example, the trigger signal may be a radio frequency signal generated by a patient activator when the patient activates a pushbutton of the patient activator.

A method is described for performing a stress test upon a heart of a patient having an implantable medical device (IMD) implanted within, wherein the IMD is adapted to receive timing information, and configurable to subject the patient to a stress test at a time specified by timing information. A method is also disclosed for performing a stress test upon a patient having an IMD implanted within, wherein the IMD is adapted to receive a signal, and configurable to subject the patient to a stress test in response to the signal.

A method is also described for reproducing an operational state of a heart of a patient having an IMD implanted within, wherein the IMD is configurable to store sensor data in a memory until a trigger signal is received, and to use the sensor data stored in the memory to reproduce the operational state of the patient's heart. The method may involve, for example, recording cardiac conditions existing within the patient during an episode of myocardial ischemia, and subsequently recreating the cardiac conditions existing in the patient during the episode of myocardial ischemia (e.g., in a physician's office at a later time).

BRIEF DESCRIPTION OF THE DRAWINGS

The invention may be understood by reference to the following description taken in conjunction with the accompanying drawings, in which like reference numerals identify similar elements, and in which.

Figure 1:
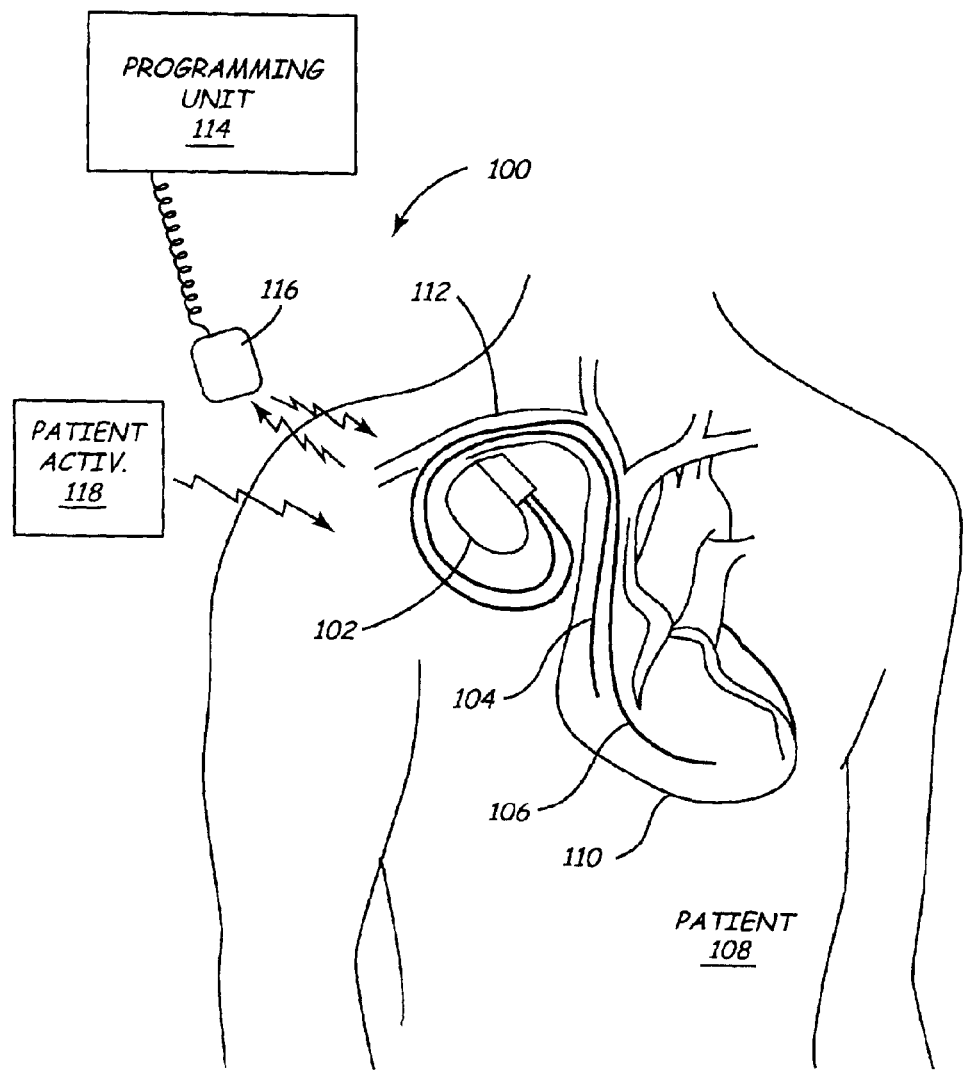
FIG. 1 is a diagram of one embodiment of an implantable medical device (IMD) system including a cardiac pacemaker, an atrial lead, and a ventricular lead implanted in a patient.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will, of course, be appreciated that in the development of any such actual embodiment, numerous implementation-specific decisions must be made to achieve the developers' specific goals, such as compliance with health-related, system-related, and business-related constraints, which will vary from one implementation to another. Moreover, it will be appreciated that such a development effort might be complex and time-consuming, but would nevertheless be a routine undertaking for those of ordinary skill in the art having the benefit of this disclosure.

FIG. 1 is a diagram of one embodiment of an implantable medical device (IMD) system 100 including a cardiac pacemaker 102, an atrial lead 104, and a ventricular lead 106 implanted in a patient 108. The pacemaker 102 produces electrical pulses (i.e., pacing pulses) that stimulate a heart 110 of the patient 108. One end of the atrial lead 104 is electrically coupled to the pacemaker 102, while the other end of the atrial lead 104 extends through a vein 112 into a right atrium of the heart 110. One end of the ventricular lead 106 is electrically coupled to the pacemaker 102, and the other end of the ventricular lead 106 extends through the vein 112 and into a right ventricle of the heart 110. Electrically conductive electrodes attached to the ends of the atrial lead 104 and the ventricular lead 106 located within the heart 110 are used to deliver pacing pulses to the heart 110. As will be described below, other electrically conductive electrodes and/or sensors attached along the lengths of the atrial lead 104 and the ventricular lead 106 are used to receive electrical signals present within the heart 110 (e.g., intrinsic depolarization signals), and to generate electrical signals indicative of conditions present within the heart 110 (e.g., intracardiac blood pressure, oxygen concentration, etc.).

It is noted that in other embodiments of the implantable medical device (IMD) system 100, the cardiac pacemaker 102 may be a cardiac defibrillator.

In the embodiment of FIG. 1, the pacemaker 102 is housed within a hermetically sealed, biologically inert outer canister or housing. At least a portion of the housing is electrically conductive, and serves as an electrode in pacing and/or sensing circuits of the pacemaker 102.

The IMD system 100 of FIG. 1 also includes a programming unit 114 for programming the pacemaker 102. A programming head 116 is connected to the programming unit 114, and enables two-way communication between the programming unit 114 and the pacemaker 102 as indicated in FIG. 1. For example, the programming head 116 may include a radio frequency (RF) antenna, and may send RF signals to, and receive RF signals from, the pacemaker 102.

The IMD system 100 of FIG. 1 also includes a patient activator 118 for sending a signal to the pacemaker 102. The patient activator 118 may include, for example, a radio frequency (RF) transmitter and a pushbutton (e.g., an electrical pushbutton switch). Pressing the pushbutton may activate the radio frequency (RF) transmitter, causing the radio frequency (RF) transmitter to transmit a radio frequency (RF) signal to the pacemaker 102. As will be described in detail below, the patient 108 may press the pushbutton when suffering myocardial ischemia, or a potentially ischemic episode. As will be described in detail below, in response to the radio frequency (RF) signal, the pacemaker 102 may stop storing sensor/lead data in a circular buffer such that data acquired prior to pushbutton activation is stored in the pacemaker 102. Alternately, the pacemaker 102 may respond to activation of the pushbutton by inserting a time stamp marker into stress test data while in a stress test mode, or exiting the stress test mode.

Figure 2:
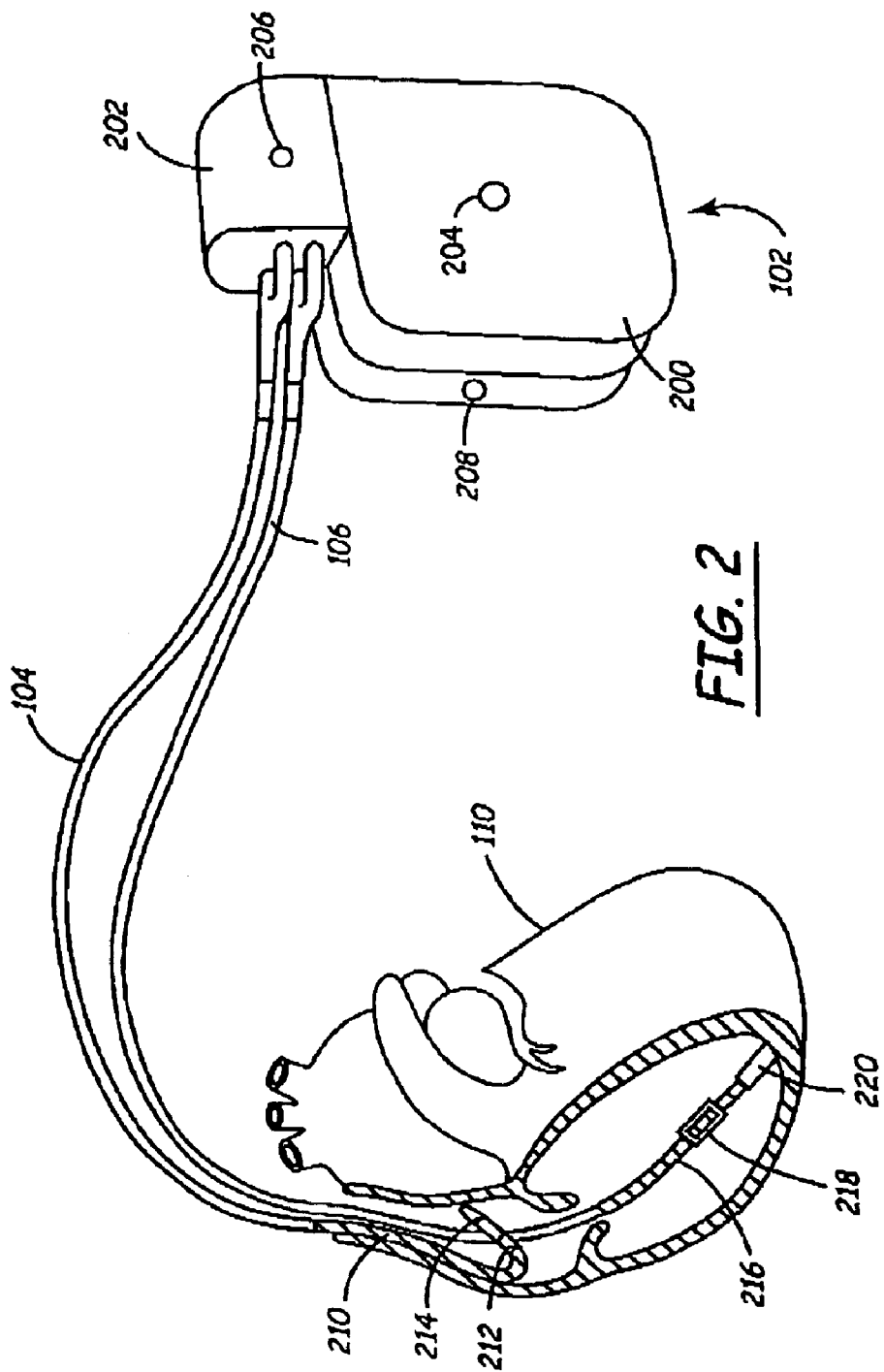
FIG. 2 is a perspective view of exemplary embodiments of the pacemaker, the atrial lead, and the ventricular lead of FIG. 1.

FIG. 2 is a perspective view of exemplary embodiments of the pacemaker 102, the atrial lead 104, and the ventricular lead 106 of FIG. 1. In the embodiment of FIG. 2, pacemaker 102 includes an electrically conductive outer housing 200 that functions as an electrode. A connector block 202 is connected to an upper portion of the housing 200, and receives one end of the atrial lead 104 and the ventricular lead 106. Three point electrodes 204, 206, and 208 are positioned on various surfaces of the housing 200 and the connector block 202, and are electrically isolated from one another and from the housing 200. In FIG. 2, the point electrode 204 is positioned near a center of a front surface of the pacemaker 102, the point electrode 208 is positioned on a left side surface of the pacemaker 102, and the point electrode 206 is positioned on a front surface of the connector block 202.

In general, the point electrodes 204, 206, and 208, and the housing 200, are used to produce one or more intrathoracic electrogram (EGM) signals. For example, the point electrodes 204, 206, and 208, and the housing 200, may be connected to inputs of multiple differential sense amplifiers within the pacemaker 102. The differential sense amplifiers may produce intrathoracic electrogram (EGM) signals at output terminals. It is noted that in other embodiments, other types of intrathoracic electrodes may be used.

In the embodiment of FIG. 2, the atrial lead 104 includes a coil electrode 210, a ring electrode 212, and a tip electrode 214. The ventricular lead 106 includes a coil electrode 216, a sensor capsule 218, and a tip electrode 220. The tip electrode 214 of the atrial lead 104 is used to deliver pacing pulses to the right atrium of the heart 110, and the tip electrode 220 of the ventricular lead 106 is used to deliver pacing pulses to the right ventricle of the heart 110. The coil electrodes 210 and 216, and the ring electrode 212, may be used to convey electrical signals present within the heart 110 (e.g., intrinsic depolarization signals) to the pacemaker 102. The sensor capsule 218 may contain one or more sensors for measuring, for example, intracardiac blood pressure, oxygen concentration, etc. In other embodiments, the element labeled 218 in FIG. 2 may be an electrode (e.g., a ring electrode), and the electrodes 210, 212, 216, and 218, may be used to used to convey electrical signals present within the heart 110 (e.g., intrinsic depolarization signals) to the pacemaker 102, and/or to generate electrical signals indicative of conditions present within the heart 110 (e.g., intracardiac blood pressure, oxygen concentration, etc.).

Figure 3:
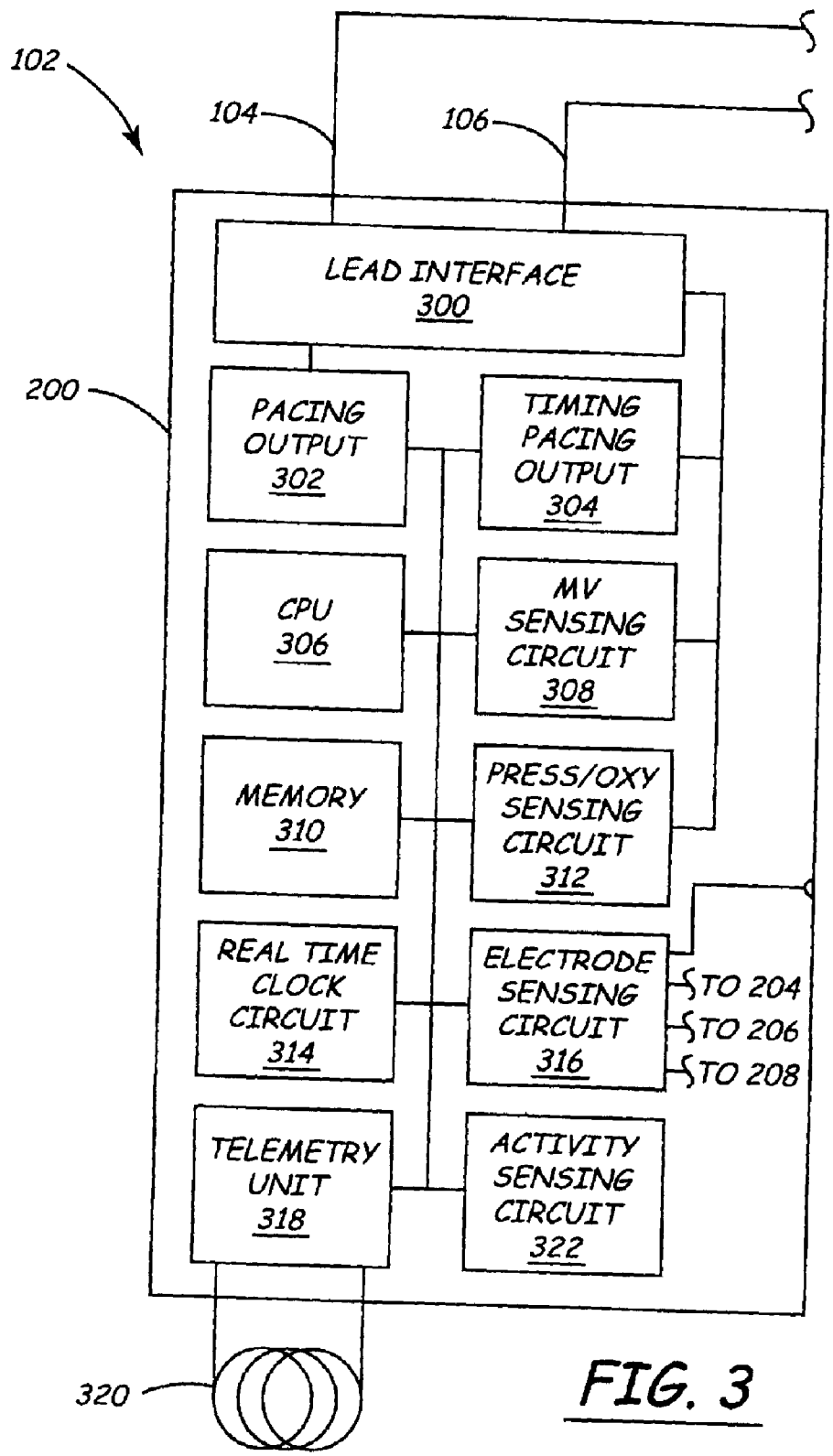
FIG. 3 is a diagram of one embodiment of the cardiac pacemaker of FIGS. 1 and 2, wherein the pacemaker includes pacing output circuitry, timing/pacing control circuitry, a central processing unit (CPU), a memory, a real time clock, an electrode sensing circuit, and a telemetry unit.

FIG. 3 is a diagram of one embodiment of the cardiac pacemaker 102 of FIGS. 1 and 2. As described above, the pacemaker 102 produces pacing pulses delivered to the heart 110 of the patient 108 (FIG. 1) via the atrial lead 104 and the ventricular lead 106. In the embodiment of FIG. 3, the pacemaker 102 includes lead interface circuitry 300, pacing output circuitry 302, timing/pacing control circuitry 304, a central processing unit (CPU) 306, a minute ventilation (MV) sensing circuit 308, a memory 310, pressure/oxygen sensing circuits 312, a real time clock 314, an electrode sensing circuit 316, a telemetry unit 318, an antenna 320, and an activity sensing circuit 322.

The atrial lead 104 and the ventricular lead 106 conduct pacing pulses produced by the pacemaker 102 to the heart 110 of the patient 108 (FIG. 1), conduct intrinsic electrical signals present within the heart 110 to the pacemaker 102, and convey electrical signals indicative of conditions present within the heart 110 (e.g., intracardiac blood pressure, oxygen concentration, etc.). The lead interface circuitry 300 forms an electrical interface between the atrial lead 104 and the ventricular lead 106 and other components of the pacemaker 102. As will be described in detail below, the pacing output circuitry 302 produces atrial and ventricular pacing pulses for stimulating the heart 110. The timing/pacing control circuitry 304 includes various registers for storing values indicative of programmed parameters of the pacemaker 102, and various counters for performing timing functions. The functions of the timing/pacing control circuitry 304 will be described in detail below. The CPU 306 executes instructions stored in the memory 310, and controls the operations of other components of the pacemaker 102.

Adapted for connecting to the atrial lead 104 and the ventricular lead 106 and capable of delivering pacing pulses to the right atrium and the right ventricle of the heart 110 (FIG. 1), the pacemaker 102 of FIGS. 1 and 2 may be termed a dual-chamber pacemaker. The pacemaker 102 may be programmable to operate in one or more of several different predefined operating modes, including a "demand" mode. In the demand mode, the pacemaker 102 senses intrinsic electrical signals present within the heart 110 of the patient 108 (FIG. 1), and produces pacing pulses only when the pacing pulses are needed. For example, the pacemaker 102 may be programmed with a value indicating whether or not the demand mode is enabled, a "low rate limit" value indicating a low limit of an intrinsic beat rate of the heart 110 of the patient 108 (FIG. 1), and an atrial-ventricular (A-V) interval value indicating a maximum length of time between an atrial contraction or "atrial beat" and a subsequent ventricular contraction or "ventricular beat."

Figure 4:
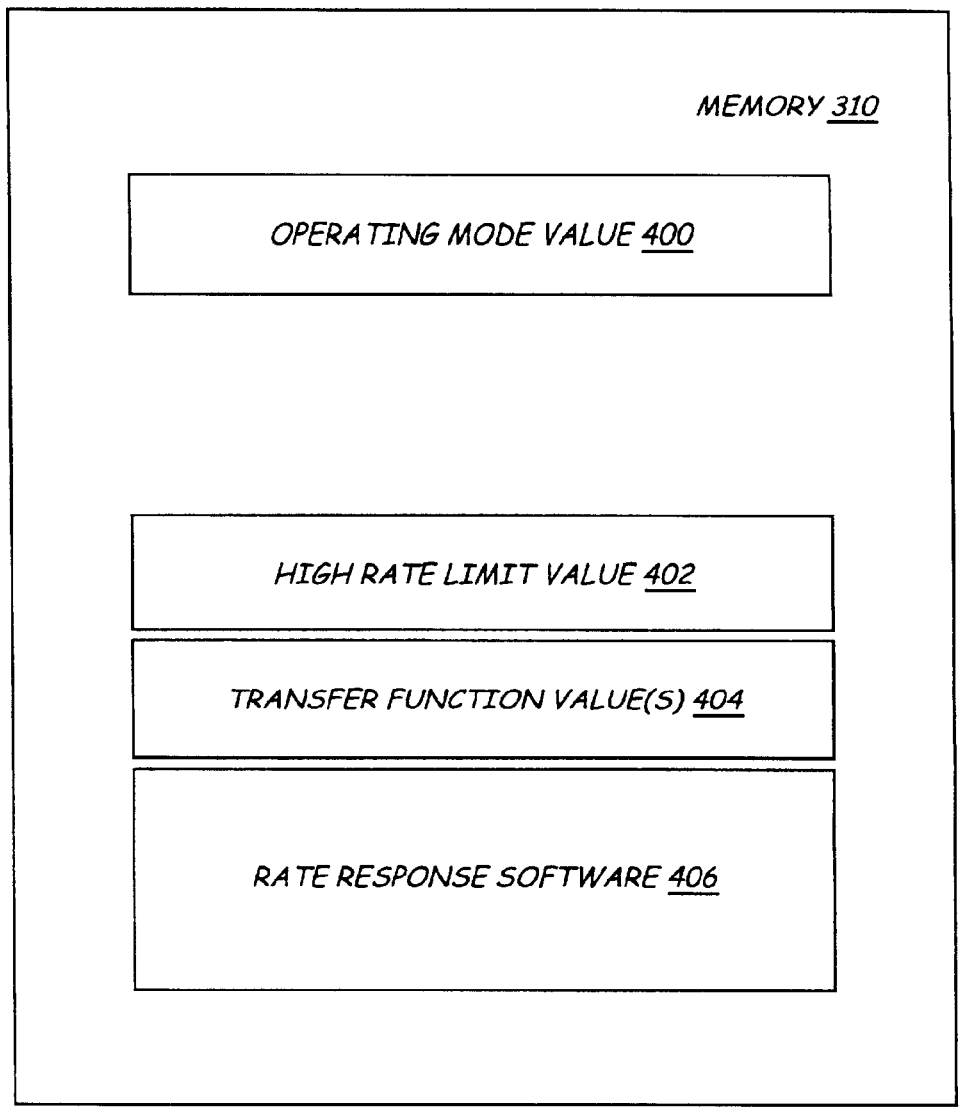
FIG. 4 is a diagram of one embodiment of the memory of FIG. 3, wherein the memory stores several values associated with a "rate response" operating mode of the pacemaker.

FIG. 4 is a diagram of one embodiment of the memory 310 of FIG. 3, wherein the memory 310 stores an operating mode value 400, a high rate limit value 402, transfer function value(s) 404, and rate response software 406. As will be described in detail below, the pacemaker 102 of FIGS. 1 and 2 is capable of operating in any one of several different operating modes, including several different test modes. The operating mode value 400 indicates a current operating mode of the pacemaker 102.

The high rate limit value 402, the transfer function value(s) 404, and the rate response software 406 are all associated with a rate response operating mode of the pacemaker 102. The operating mode value 400 indicates whether the pacemaker 102 is operating in the rate response operating mode. The rate response operating mode of the pacemaker 102 may be enabled by programming the operating mode value 400 (e.g., via the programming unit 114 of FIG. 1). In the rate response operating mode, the CPU 306 executes software instructions of the rate response software 406. As will be described in detail below, the high rate limit value 402 indicates a high rate limit of a paced beat rate of the heart 110 of the patient 108 in the rate response operating mode.

Figure 5:
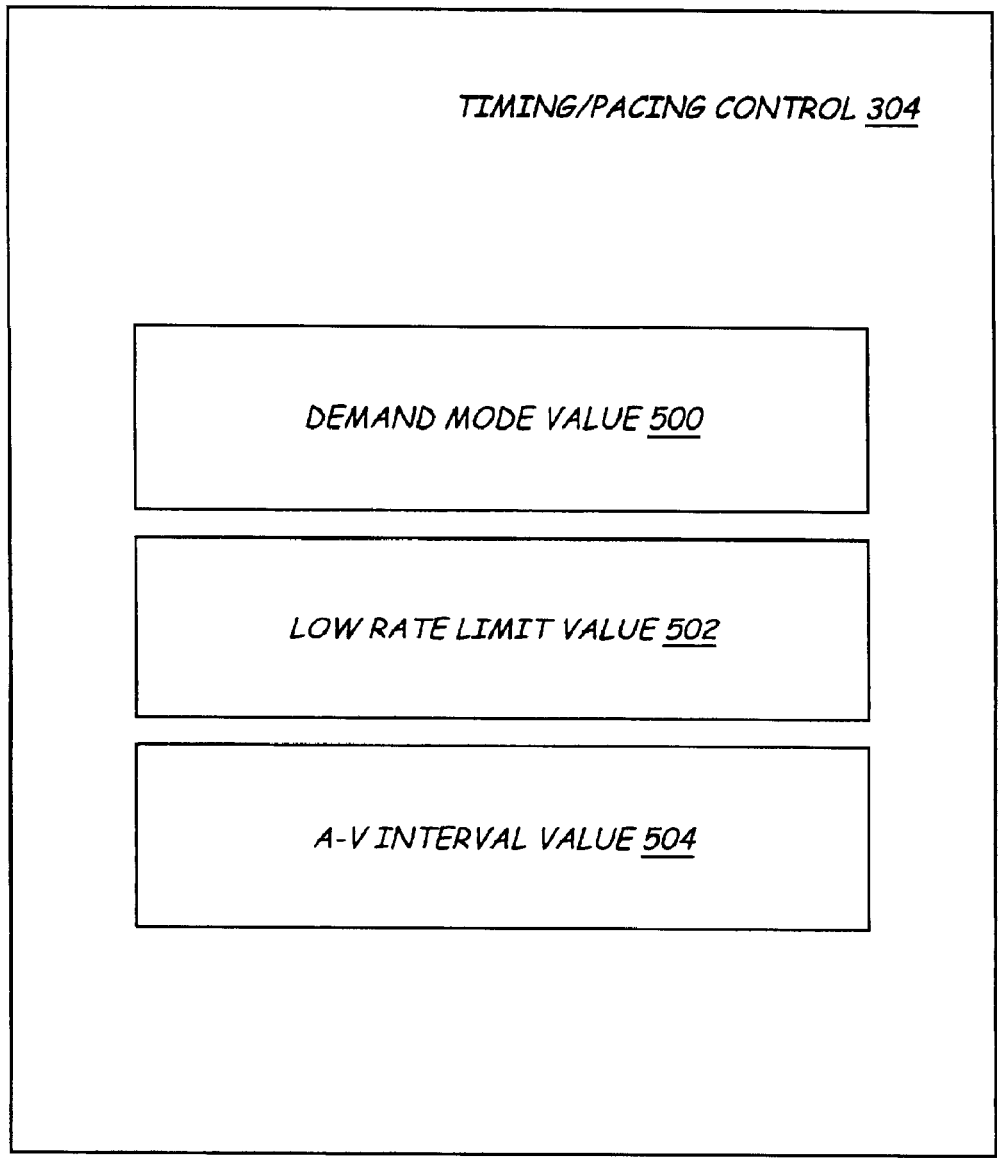
FIG. 5 is a diagram of one embodiment of the timing/pacing control circuitry of FIG. 3, wherein the timing/pacing control circuitry includes means for storing several values associated with a "demand" operating mode of the pacemaker.

FIG. 5 is a diagram of one embodiment of the timing/pacing control circuitry 304 of FIG. 3. In the embodiment of FIG. 5, the timing/pacing control circuitry 304 includes a demand mode value 500, a low rate limit value 502, and an atrial-ventricular (A-V) interval value 504 (e.g., stored in one or more registers of the timing/pacing control circuitry 304). The timing/pacing control circuitry 304 also provides intracardiac electrogram (EGM) waveform data to the CPU 306.

The timing/pacing control circuitry 304 includes sensing circuitry that receives and detects intrinsic electrical signals present within the heart 110 of the patient 108 (FIG. 1). Specifically, the sensing circuitry of the timing/pacing control circuitry 304 receives a first electrical signal indicative of an intrinsic contraction of the right atrium via the atrial lead 104. In response to the first electrical signal, the sensing circuitry may generate an "atrial beat" signal within the timing/pacing control circuitry 304.

The demand mode value 500 indicates whether or not the demand mode of the pacemaker 102 is enabled. The low rate limit value 502 indicates a low rate limit of the paced beat rate of the heart 110 (FIG. 1). In the demand mode, the timing/pacing control circuitry 304 may provide an atrial trigger signal to the pacing output circuitry 302 if a frequency at which the atrial beat signals are generated is below the low rate limit indicted by the low rate limit value 502. In response to the atrial trigger signal, the pacing output circuitry 302 may produce an atrial pacing pulse, and provide the atrial pacing pulse to the right atrium of the heart 110 (FIG. 1) via the atrial lead 104. The atrial pacing pulse typically causes the right and left atria of the heart 110 to contract in unison.

The sensing circuitry of the timing/pacing control circuitry 304 also receives a second electrical signal indicative of an intrinsic contraction of the right ventricle via the ventricular lead 106. In response to the second electrical signal, the sensing circuitry may generate a ventricular beat signal within the timing/pacing control circuitry 304. The A-V interval value 504 indicates a desired A-V interval. In the demand mode, if the ventricular beat signal is not generated within the desired A-V interval indicated by the A-V interval value 504 following an atrial beat signal, the timing/pacing control circuitry 304 may provide a "ventricular trigger" signal to the pacing output circuitry 302. In response to the ventricular trigger signal, the pacing output circuitry 302 may produce a ventricular pacing pulse, and provide the ventricular pacing pulse to the right ventricle of the heart 110 (FIG. 1) via the ventricular lead 106. The ventricular pacing pulse typically causes the right and left ventricles of the heart 110 to contract in unison.

The minute ventilation sensing circuit 308 produces a minute ventilation output signal indicative of the minute ventilation of the patient 108 (FIG. 1). It is noted that there are several known methods for producing measures of minute ventilation of the patient 108 (FIG. 1), any one of which may be employed by the minute ventilation sensing circuit 308 to produce the minute ventilation output.

The minute ventilation output signal may also be indicative a respiration rate of the patient 108, and/or a tidal volume of the patient 108. For example, the minute ventilation sensing circuit 308 may produce the minute ventilation output signal dependent upon changes of electrical impedance in a thoracic cavity of the patient 108. It is well known that such a thoracic impedance signal has an alternating current (a.c.) component having a frequency indicative of a respiration rate to the patient 108 (FIG. 1), and a peak-to-peak amplitude indicative of a tidal volume of the patient 108. The thoracic impedance signal may be sampled at regular intervals, and the analog samples may be converted to corresponding digital values. The minute ventilation output signal may thus include digital values produced at regular time intervals and indicative of not only the minute ventilation of the patient 108, but also the respiration rate and/or the tidal volume of the patient 108. Alternately, the minute ventilation output signal may be a continuous analog signal.

The activity sensing circuit 322 senses movement or physical activity of the patient 108 (FIG. 1), and produces an "activity output" indicative of a magnitude of the movement or physical activity of the patient 108. In one embodiment, the "activity output" constitutes digital "activity values" produced at regular time intervals. In other embodiments, the activity output may be a continuous analog signal.

It is noted that there are several known methods for producing measures of movement or physical activity of the patient 108 (FIG. 1), any one of which may be employed by the activity sensing circuit 322 to produce the activity output.

In the rate response operating mode, the CPU 306 (FIG. 3) may execute software instructions of the rate response software 406 (FIG. 4) as described above. In the rate response operating mode, the CPU 306 may vary the low rate limit value 502 and/or the A-V interval value 504 stored in the timing/pacing control circuitry 304, dependent upon the minute ventilation output produced by the MV sensing circuit 308 and/or the activity output produced by the activity sensing circuit 322. The transfer function value(s) 404 (FIG. 4) indicates a desired transfer function. The CPU 306 may vary the low rate limit value 502 and/or the A-V interval value 504 according to the desired transfer function indicated by the transfer function value(s) 404 to achieve a desired rate response. The desired rate response is defined by the low rate limit value 502, the high rate limit value 402, and the transfer function value(s) 404. The rate at which the pacing output circuitry 302 produces the atrial pacing pulses is varied between the low rate limit, indicated by the low rate limit value 502, and the high rate limit, indicated by the high rate limit value 402, dependent upon the minute ventilation output produced by the MV sensing circuit 308 and/or the activity output produced by the activity sensing circuit 322. For example, a "target" pacing rate at which pacing output circuitry 302 produces the atrial pacing pulses may be expressed as:

target pacing rate=low rate limit+$f$(sensing circuit output)

where $f$ is a linear or monotonic function of the minute ventilation output produced by the MV sensing circuit 308 and/or the activity output produced by the activity sensing circuit 322.

For example, when the activity output produced by the activity sensing circuit 322 indicates that an activity level of the patient 108 (FIG. 1) has increased, the target pacing rate may be increased from the low rate limit indicated by the low rate limit value 502 by incremental amounts determined by the activity output produced by the activity sensing circuit 322. As long as the activity output produced by the activity sensing circuit 322 indicates activity of the patient 108, the target pacing rate may be periodically increased by incremental amounts until the high rate limit, indicated by the high rate limit value 402, is reached. When the activity output produced by the activity sensing circuit 322 indicates activity of the patient 108 has ceased, the target pacing rate may be gradually reduced by incremental amounts until the low rate limit indicated by the low rate limit value 502 is reached.

The rate response function $f$ is preferably selected such that the target pacing rate is based on a combination of the outputs of the activity sensing circuit 322 and the minute ventilation sensing circuit 308. For example, the rate response function $f$ may be selected such that the target pacing rate is based substantially on the activity output produced by the activity sensing circuit 322 when the patient is relatively inactive, and based substantially on the minute ventilation output produced by the minute ventilation sensing circuit 308 when the patient is relatively active. Any one of several known methods for combining or "blending" outputs of activity sensors and minute ventilation sensors may be employed in generating the target pacing rate.

The telemetry unit 318 is coupled to the antenna 320, and communicates with the programming head 116 (FIG. 1) via antenna 320. For example, the antenna 320 may be a radio frequency (RF) antenna, and the telemetry unit 318 may send RF signals to, and receive RF signals from, the programming head 116 (FIG. 1). In the embodiment of FIGS. 1 and 3, CPU 306 communicates with the programming unit 114 (FIG. 1) via the telemetry unit 318, the antenna 320, and the programming head 116. CPU 306 receives values to be stored in memory locations of the memory 310 from the programming unit 114 via the telemetry unit 318. The received values may be, for example, the values of programmable parameters which determine the operation of the pacemaker 102. CPU 306 may also use the telemetry unit 318 to transmit values residing in memory locations of the memory 310 to the programming unit 114. The transmitted values may be, for example, the values of programmable parameters which determine the operation of the pacemaker 102, and/or data indicative of sensed parameters of the patient 108 (FIG. 1).

Figure 6:
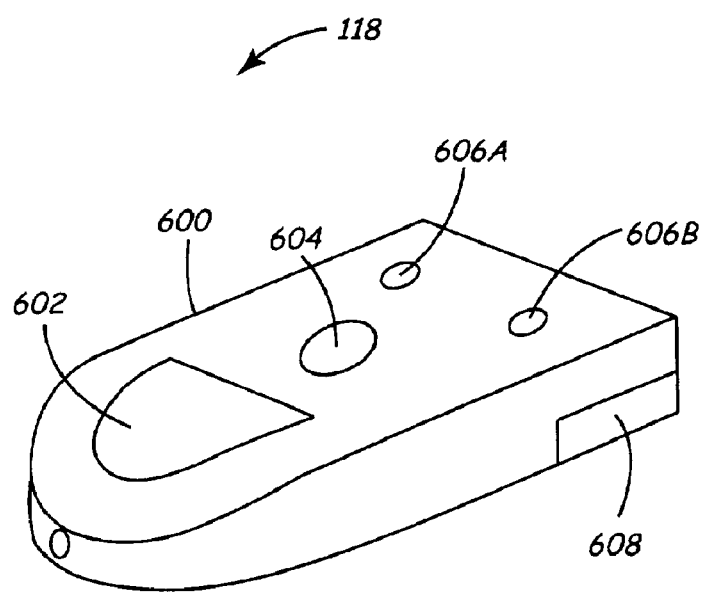
FIG. 6 is a perspective view of one embodiment of the patient activator of FIG. 1, wherein the patient activator includes a pushbutton.

FIG. 6 is a perspective view of one embodiment of the patient activator 118 of FIG. 1. In the embodiment of FIG. 6, the patient activator 118 includes an enclosure 600, a pushbutton 602, a speaker 604, light-emitting diodes (LEDs) 606A and 606B, and a battery compartment cover 608. The pushbutton 602, the speaker 604, and the LEDs 606A–606B are arranged upon an upper surface of the enclosure 600. The battery compartment cover 608 forms a portion of an underside surface of the enclosure 600, and provides access to a battery compartment.

Figure 7:
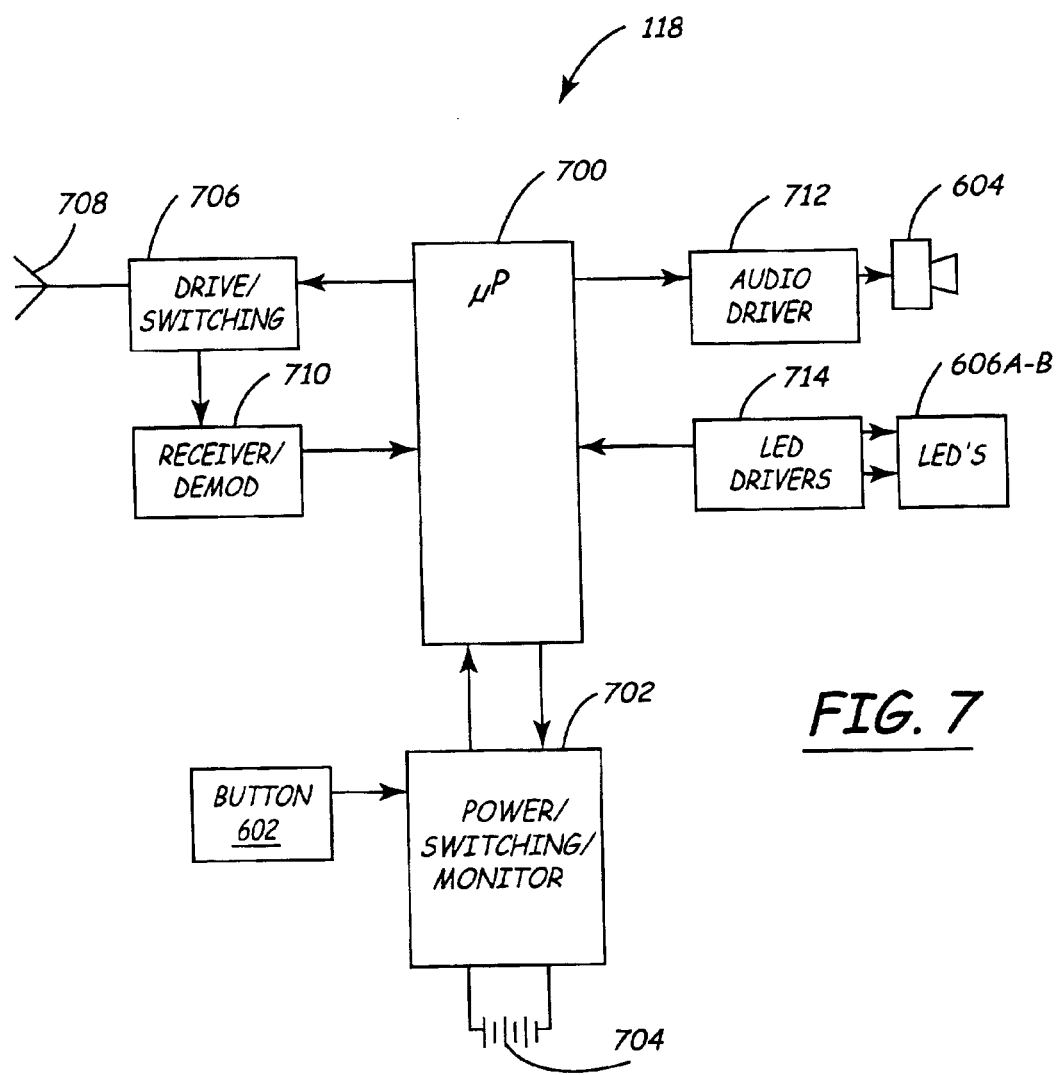
FIG. 7 is a diagram of one embodiment of the patient activator of FIG. 6, wherein the patient activator includes means for generating a signal when the pushbutton is activated.

FIG. 7 is a diagram of one embodiment of the patient activator 118 of FIG. 6. In the embodiment of FIG. 7, the patient activator 118 includes a microprocessor (uP) 700, a power/switching/monitor circuit 702, a battery 704, an antenna drive/switching circuit 706, a radio frequency (RF) antenna 708, a receiver/demodulator 710, an audio driver 712, and light-emitting diode (LED) drivers 714. The microprocessor 700 controls the other components of the patient activator 118 based upon programming instructions stored in a memory (not shown). The audio driver 712 is coupled between the microprocessor 700 and the speaker 604 (FIG. 6). The microprocessor 700 provides output signals for producing audible patient alert signals via the audio driver 712 and the speaker 604. The LED drivers 714 are coupled between the microprocessor 700 and the LEDs 606A–B (FIG. 6). The microprocessor 700 provides control signals to the LED drivers 714 to light the LEDs 606A–B. The battery 704 provides electrical power for the patient activator 118, and is coupled to the microprocessor 700 via the power/switching/battery monitor circuit 702. The power/switching/battery monitor circuit 702 also provides the microprocessor 700 with an indication that the pushbutton 602 has been activated (i.e., pressed).

Communication between the patient activator 118 and the pacemaker 102 (FIGS. 1 and 2) is accomplished via the antenna drive/switching circuit 706, the radio frequency (RF) antenna 708, and the receiver/demodulator 710. Radio frequency (RF) transmissions from the pacemaker 102 are received by the RF antenna 708, demodulated by the receiver/demodulator 710, and provided to the microprocessor 700. The microprocessor 700 controls operations of the audio driver 712 and the LED drivers 714 dependent upon RF transmissions received from the pacemaker 102. In RF transmissions from the patient activator 118 to the pacemaker 102 (e.g., in response to activation of the pushbutton 602), the microprocessor 700 provides transmission control and data signals to the antenna drive/switching circuit 706. The antenna drive/switching circuit 706 drives the RF antenna 708 dependent upon the transmission control and data signals.

Figure 8:
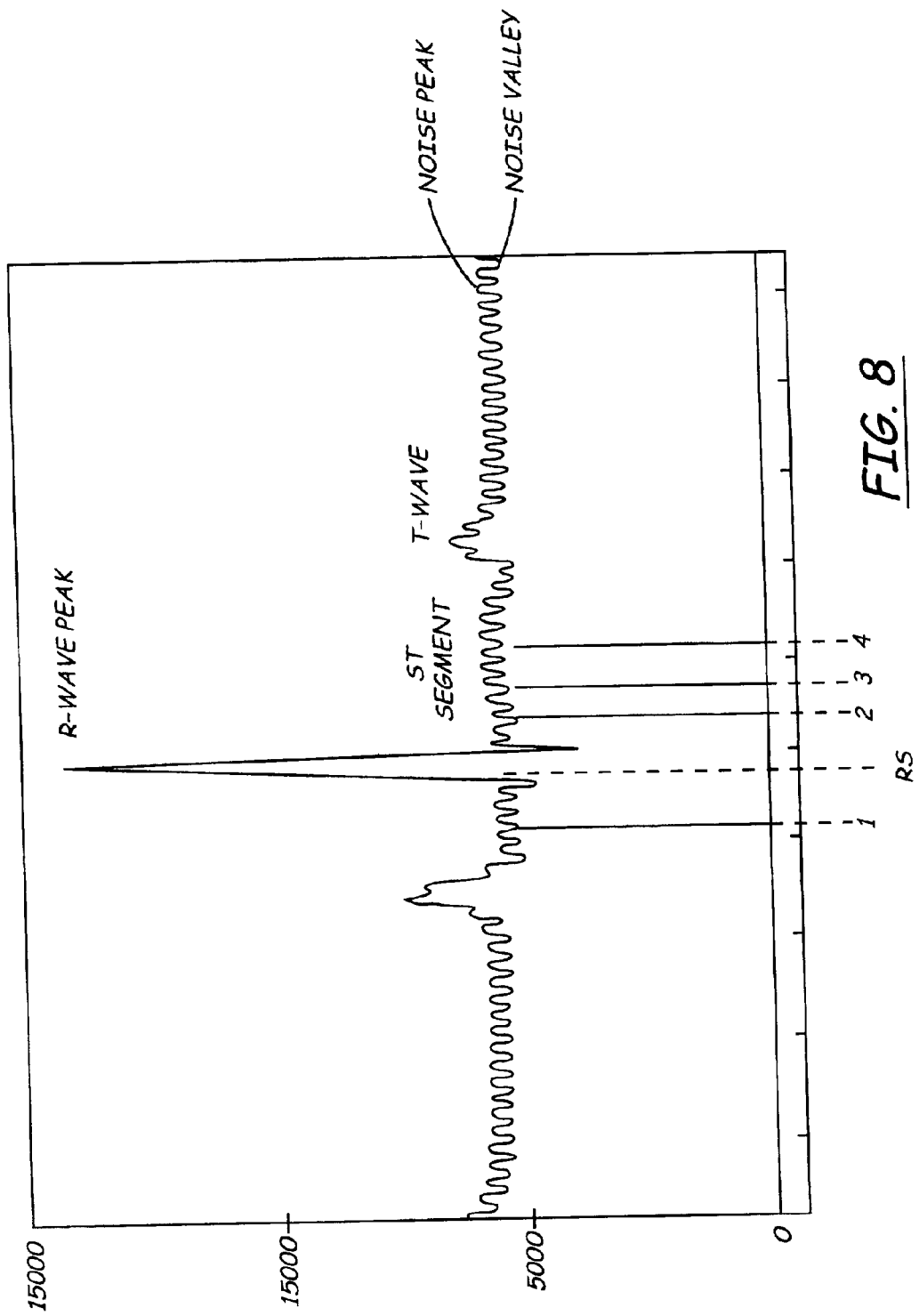
FIG. 8 is an exemplary electrogram (EGM) waveform produced within the patient of FIG. 1, wherein the patient shows no signs of ST segment deviation indicative of myocardial ischemia.
Figure 9:
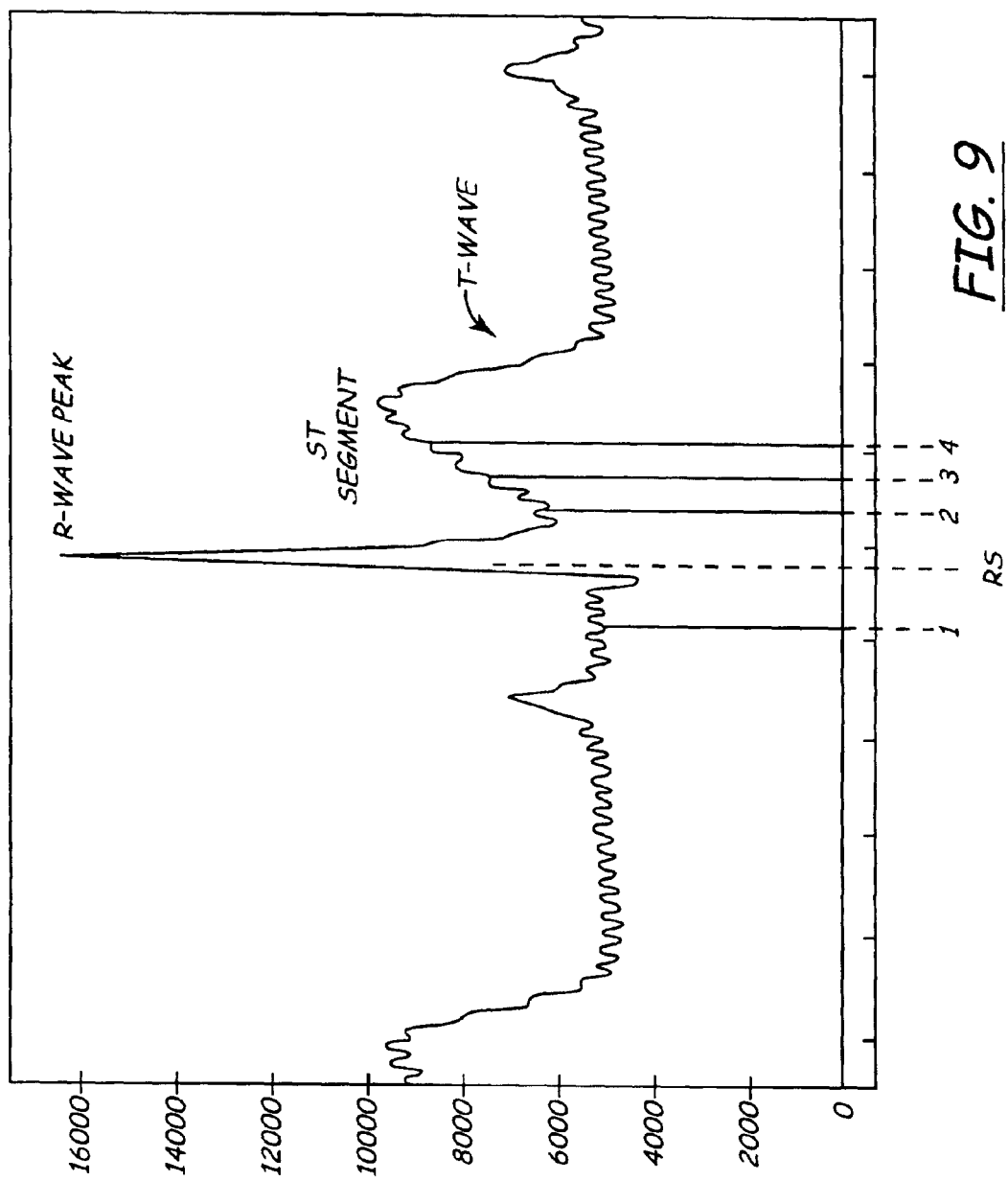
FIG. 9 is an exemplary electrogram (EGM) waveform produced within the patient of FIG. 1, wherein the patient shows ST segment deviation indicative of myocardial ischemia.

FIGS. 8 and 9 will now be used to illustrate how ST segment deviation in an electrogram (EGM) waveform may be used to detect myocardial ischemia. As described above in connection with FIG. 2, the point electrodes 204, 206, and 208, and the housing 200, may be used to produce intrathoracic electrogram (EGM) waveforms. The electrodes on the atrial lead 104 and/or the ventricular lead 106 (FIGS. 1–2) may be used to produce intracardiac electrogram (EGM) waveforms. The electrogram (EGM) waveforms used to detect myocardial ischemia may include the intrathoracic electrogram (EGM) waveforms produced using the point electrodes 204, 206, and/or 208 of FIG. 2. Alternately, or in addition, the electrogram (EGM) waveforms used to detect myocardial ischemia may include the intracardiac electrogram (EGM) waveforms produced using the electrodes on the atrial lead 104 and/or the ventricular lead 106 (FIGS. 1–2).

FIG. 8 is an exemplary electrogram (EGM) waveform produced within the patient 108 (FIG. 1), wherein the patient 108 shows no signs of ST segment deviation indicative of myocardial ischemia. The electrogram (EGM) waveform of FIG. 8 includes a P-wave preceding a QRS complex in time, a T-wave following the QRS complex in time, and an ST segment residing between the S-wave of the QRS complex and the T-wave. In the non-ischemic electrogram (EGM) waveform of FIG. 8, the ST segment does not deviate substantially from a baseline of the electrogram (EGM) waveform.

The points on the electrogram (EGM) waveform labeled 1, 2, 3, and 4 in FIG. 8 indicate waveform sampling points for an ST segment analysis algorithm that may be used to determine ST segment deviation. See, for example, U.S. Pat. No. 6,128,526, incorporated herein by reference in its entirety. The R-wave peak may be used as a time reference point (i.e., a fiducial point). When an R-wave peak is detected, the sample points 1, 2, 3, and 4 may be determined relative to the R-wave peak. The amplitude of the electrogram (EGM) waveform at sample point 1, preceding the QRS complex, may be used to establish an isoelectric or baseline level of the electrogram (EGM) waveform. It is noted that in the non-ischemic electrogram (EGM) waveform of FIG. 8, disparities between amplitudes of the electrogram (EGM) waveform at sample points 1, 2, 3, and 4 are relatively small.

FIG. 9 is an exemplary electrogram (EGM) waveform produced within the patient 108, wherein the patient 108 shows ST segment deviation indicative of myocardial ischemia. In the ischemic electrogram (EGM) waveform FIG. 9, both the ST segment and the T-wave are elevated above the respective amplitudes in FIG. 8, and the ST segment deviates substantially from a baseline of the electrogram (EGM) waveform. In contrast to the non-ischemic electrogram (EGM) waveform of FIG. 8, the disparities between the amplitudes of the ischemic electrogram (EGM) waveform of FIG. 9 at sample points 1, 2, 3, and 4 are relatively large.

While ST segment deviations from isoelectric baselines are readily detectable in electrogram (EGM) waveforms, several other changes are also known to occur in electrogram (EGM) waveforms as a result of myocardial ischemia. It is noted that any one of these other known changes may also be used to detect myocardial ischemia within the patient 108.

It is also noted that the electrogram (EGM) waveforms of FIGS. 8 and 9 include low amplitude 50/60 Hz alternating current (ac) noise components imposed by nearby 50/60 Hz electrical power distribution systems. It is desirable to reduce the amplitudes of these 50/60 Hz noise components as much as possible prior to ST segment analysis.

Figure 10:
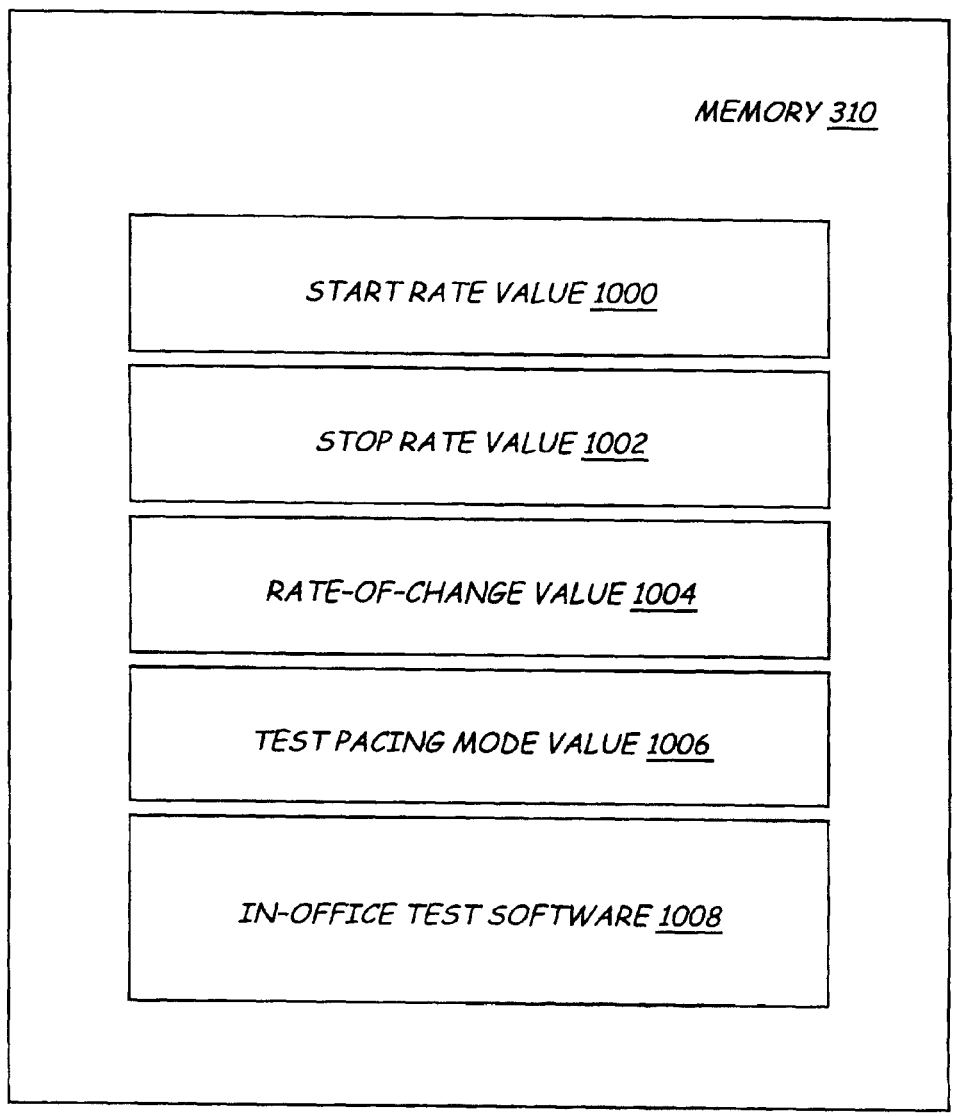
FIG. 10 shows data and instructions stored in the memory of the pacemaker of FIGS. 1–3 and associated with an in-office stress test operating mode.
Figure 11A:
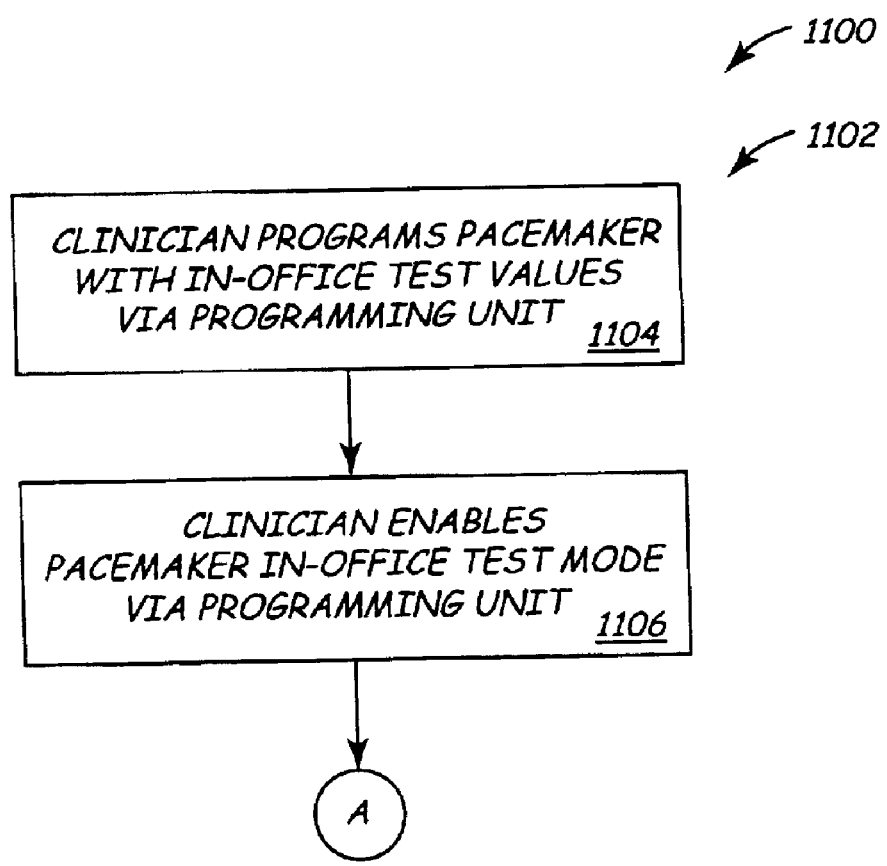
FIGS. 11A and 11B in combination form a flow chart illustrating one embodiment of a method for subjecting the patient of FIG. 1 to a stress test (e.g., an "in-office" stress test) using the implantable medical device (IMD) system of FIG. 1.
Figure 11B:
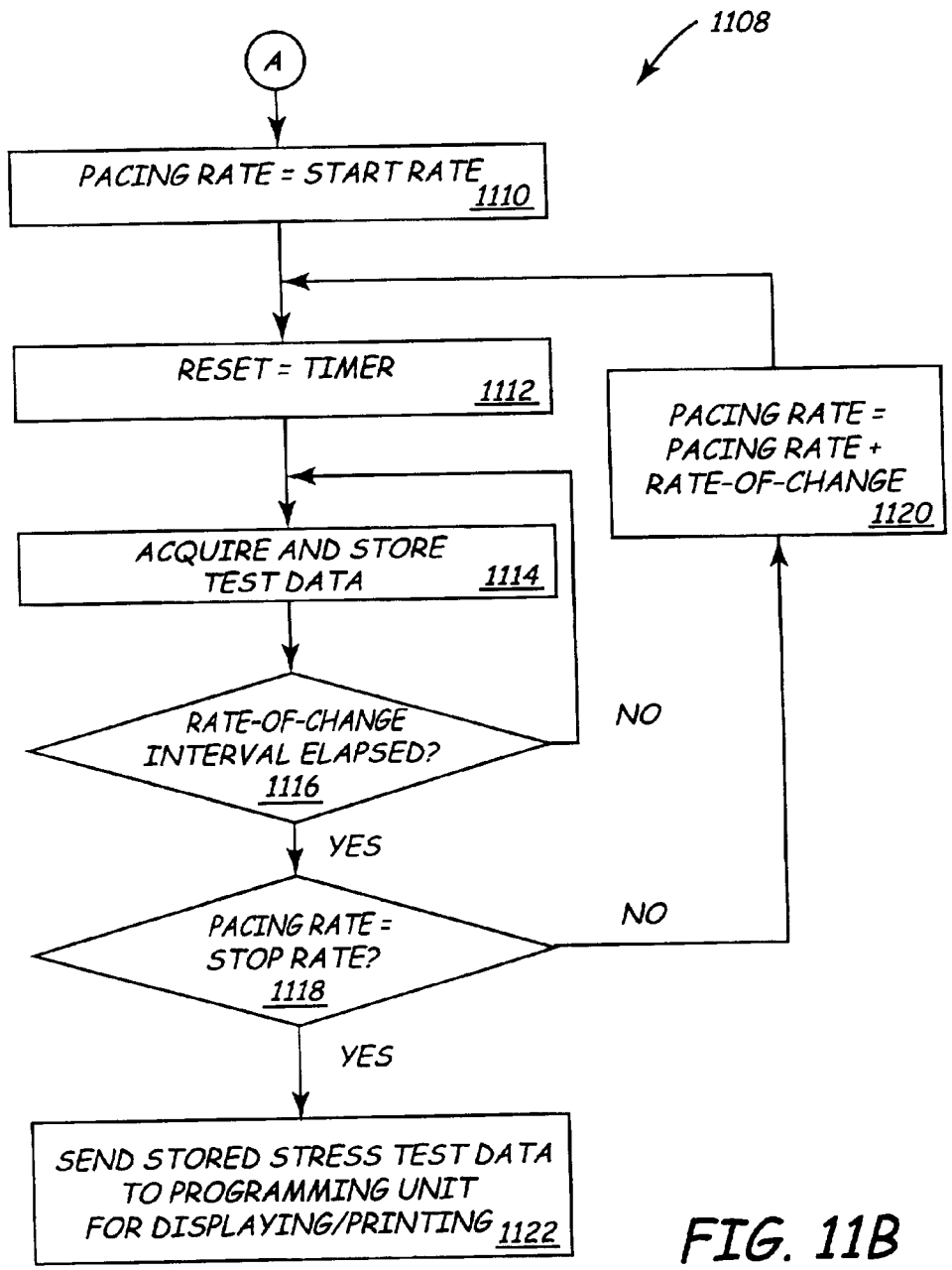

FIGS. 10 and 11A–B will now be used to describe an "in-office stress test" operating mode of the pacemaker 102 of FIGS. 1–3. The in-office stress test operating mode subjects the patient 108 (FIG. 1) to a stress test, during which the pacemaker 102 is used to gradually increase the rate at which the heart 110 (FIG. 1) of the patient 108 beats from a start rate to a stop rate, wherein the stop rate is greater than the start rate. During an initial portion of the stress test, the heart rate of the patient 108 is increased in a linear or monotonic fashion from the start rate to the stop rate. During a final portion of the stress test, the heart rate of the patient 108 is decreased in a linear or monotonic fashion from the stop rate to the start rate. The stress test is intended to be accomplished while the patient 108 is in a physician's office, and will therefore be referred to as an "in-office stress test" herein below. During the in-office stress test, the programming head 116 (FIG. 1 ) may be positioned in proximity of the pacemaker 102, and the pacemaker 102 may transmit lead/sensor data to the programming unit 114 (FIG. 1) for display and/or analysis.

FIG. 10 shows data and instructions stored in the memory 310 (FIG. 3) of the pacemaker 102 and associated with the in-office stress test operating mode. It should be noted that data instructions for the in-office stress test may be resident in external devices such as programmer unit 114, patient activator 118 and similar other devices in operational relations with pacemaker 102. Accordingly, the disclosure herein referring to the in-office stress test data and instructions being resident in pacemaker 102 is for illustrative purposes and does not limit the location of the operative software and controls for the in-office stress test. In the embodiment of FIG. 10, the memory 310 includes a start rate value 1000, a stop rate value 1002, a rate-of-change value 1004, a test pacing mode value 1006, and in-office stress test software 1008. The start rate value 1000 specifies a starting pacing rate at which the pacemaker 102 paces the heart 100 of the patient 108 at a beginning of the in-office stress test.

The stop rate value 1002 specifies a maximum pacing rate at which the pacemaker 102 paces the heart 100 of the patient 108 during the in-office stress test.

The rate-of-change value 1004 specifies a rate at which the pacemaker 102 increases the heart rate of the patient 108 during the in-office stress test. The rate-of change value 1004 reflects a "linear acceleration" embodiment of the invention. For example, the rate-of-change value 1004 may correspond to "5 beats per minute (bpm)/30 sec.", and may specify that the pacemaker 102 is to increase the heart rate of the patient 108 by 5 beats per minute (bpm) every 30 seconds during the in-office stress test.

The test pacing mode value 1006 indicates the pacing mode to be implemented by the pacemaker 102 during the in-office stress test (e.g., DDD, AAI, etc.). For example, operating mode value 400 (FIG. 4) may indicate that the pacemaker 102 is to implement a DDD operating mode. During an in-office stress test, however, the test pacing mode value 1006 may take priority over the operating mode value 400, and the pacemaker 102 may implement an AAI (atrium only) pacing mode during the in-office stress test in accordance with the test pacing mode value 1006. The in-office stress test software 1008 includes instructions and data used by the CPU 306 (FIG. 3) to implement the in-office stress test.

FIGS. 11A and 11B in combination form a flow chart illustrating one embodiment of a method 1100 for subjecting the patient 108 (FIG. 1) to a stress test using the implantable medical device (IMD) system 100 of FIG. 1. Intended to be accomplished while the patient 108 is in a physician's office, the stress test is referred to as an "in-office stress test."

In FIG. 11A, a first portion 1102 of the method 1100 is typically performed by a clinician (e.g., in a physician's office). During a step 1104 of the portion 1102, the clinician programs the pacemaker 102 (FIGS. 1 and 2) with in-office test values using the programming unit 114 (FIG. 1). Referring back to FIG. 10, the in-office test values include the start rate value 1000, the stop rate value 1002, and the rate-of-change value 1004. During a step 1106 of the portion 1102, the clinician enables the in-office test mode of the pacemaker 102 (e.g., by programming the test pacing mode value 1006 via the programming unit 114).

FIG. 11B shows the steps of a second portion 1108 of the method 1100, which may be implemented by the in-office stress test software 1008 of FIG. 10. During a step 1110 of the portion 1108, the rate at which the pacemaker 102 paces the heart 110 of the patient 108 (FIGS. 1 and 2) is set to the start rate value 1000 (FIG. 10). A timer within the pacemaker 102 (e.g., within the CPU 306, the real time clock circuit 314, or the timing/pacing control unit 304 of FIG. 3) is reset during a step 1112.

During a step 1114, the pacemaker 102 acquires and stores stress test data. The stress test data may include, for example, intrathoracic electrogram (EGM) waveform samples produced using the point electrodes 204, 206, and/or 208 shown in FIG. 2. The stress test data may also include intracardiac electrogram (EGM) waveform samples produced using the electrodes on the atrial lead 104 and/or the ventricular lead 106 (FIGS. 1–2). The stress test data may also include measurements of ST segment deviation as described above, sensor data, pacing threshold data, arrhythmia data, and/or tissue-to-lead impedance data.

The sensor data may include, for example, intracardiac blood pressure and/or oxygen concentration data produced by the blood pressure/oxygen concentration sensing circuits 312 in FIG. 3, respiration rate and/or minute ventilation data produced by the minute ventilation sensing circuit 308 in FIG. 3, and/or activity data produced by the activity sensing circuit 322 in FIG. 3. The pacing threshold data may indicate the amount of electrical energy dissipated by the pacing unit 302 while pacing the heart 110 of the patient 108 during the in-office stress test, and may be produced by the pacing unit 302. The arrhythmia data may indicate, for example, cardiac arrhythmias sensed by the pacemaker 102 (e.g., atrial/ventricular fibrillation, ventricular tachycardia, premature ventricular contractions, etc.).

As described above, the rate-of-change value 1004 (FIG. 10) specifies a rate at which the pacemaker 102 increases the heart rate of the patient 108 during the in-office stress test. The rate-of-change value 1004 conveys both a number of beats per minute (bpm) the heart rate of the patient 108 is to be increased, and a "rate-of-change interval" between heart rate increases. For example, the rate-of-change value 1004 may correspond to "5 beats per minute (bpm)/30 sec.", and thus specify that the pacemaker 102 is to increase the heart rate of the patient 108 by 5 beats per minute (bpm) every 30 seconds during the in-office stress test. In this situation, the number of beats per minute (bpm) the heart rate of the patient 108 is to be increased is 5 bpm, and the rate-of-change interval conveyed by the rate-of-change value 1004 is 30 seconds.

While the pacemaker 102 is acquiring and storing stress test data, the pacemaker 102 is also checking the timer to determine whether the rate-of-change interval has elapsed (during a step 1116). For example, the CPU 306 (FIG. 3) may be controlling the acquiring and storing of the stress test data while executing the instructions of the in-office stress test software 1008. At the same time, the CPU 306 may be polling the timer periodically to determine whether the rate-of-change interval specified by the rate-of-change value 1004 has elapsed, or waiting for an interrupt signal from the timer which indicates the rate-of-change interval has elapsed.

When the rate-of-change interval has elapsed, the pacemaker 102 checks to see if the current pacing rate is equal to the stop rate value 1002 (during a step 1118). If the current pacing rate is not equal to the stop rate value 1002, the in-office stress test is not yet complete. In this situation, the pacing rate is increased during a step 1120, and the steps 1112, 1114, 1116, and 1118 are repeated. During the step 1120, the pacing rate is increased to the current pacing rate plus the number of beats per minute (bpm) specified by the rate-of-change value 1004. If the current pacing rate is equal to the stop rate value 1002 during the step 1118, the pacemaker 102 performs a step 1122. During the step 1122, the pacemaker 102 sends the stress test data, acquired and stored during the in-office stress test, to the programming unit 114 (FIG. 1) for display and/or printing.

In order to avoid an abrupt change in the heart rate of the patient 108 at the beginning of the in-office stress test, the pacemaker 102 may check to make sure a current heart rate of the patient 108 does not differ substantially from the start rate value 1000 (FIG. 10) prior to pacing the heart 110 of the patient 108 at the start rate value 1000 (FIG. 10) during the step 1110. For example, if the current heart rate of the patient 108 prior to the step 1110 is substantially greater than the start rate value 1000, the step 1110 may be delayed until the current heart rate of the patient 108 slows and falls below the start rate value 1000 for a period of time (e.g., 30 seconds).

After the heart 110 of the patient 108 has been paced by the pacemaker 102 at the maximum rate indicated by the stop rate value 1002 for an entire rate-of-change interval, the pacing rate is decreased linearly or monotonically over a period of time from the maximum rate indicated by the stop rate value 1002 to the rate indicated by the start rate value 1000. For example, a second rate-of-change value (not shown) stored within the memory 310 (FIG. 3) may specify a rate at which the pacemaker 102 is to decrease the heart rate of the patient 108 during a final portion of the in-office stress test. The second rate-of-change value may convey both a number of beats per minute (bpm) the heart rate of the patient 108 is to be decreased, and a "rate-of-change interval" between heart beats increases. For example, the second rate-of-change value may correspond to "30 beats per minute (bpm)/60 sec.", and thus specify that the pacemaker 102 is to decrease the heart rate of the patient 108 by 30 beats per minute (bpm) every 60 seconds during the final portion of the in-office stress test.

It is noted that during the in-office stress test, the stress test may be aborted by the clinician (e.g., by clearing the test pacing mode value 1006 of FIG. 10 via the programming unit 114). In addition, the pacemaker 102 may be configured to respond to a signal from the patient activator 118 (FIGS. 1 and 6) indicating activation of a pushbutton of the patient activator (e.g., the pushbutton 602 of FIG. 6). The patient 108 may be instructed to press the pushbutton 602 of the patient activator 118 when in distress (e.g., when suffering from a sign of myocardial ischemia). A first activation of the pushbutton 602 by the patient 108 during the in-office stress test may result in inclusion of a time stamp marker in the stress test data, and a subsequent second activation of the pushbutton 602 during the in-office stress test may cause the pacemaker 102 to abort the ambulatory stress test.

Further, the pacemaker 102 may be configured to respond to a trigger signal, produced within the pacemaker 102 and indicating detected myocardial ischemia within the patient 108 during the in-office stress test, by aborting the stress test. For example, the pacemaker 102 may include myocardial ischemia detection software stored in the memory 310 (described below). The myocardial ischemia detection software may be executed by the CPU 306 (FIG. 3) during the in-office test, and the myocardial ischemia detection software may produce a trigger signal when myocardial ischemia is detected in the patient 108 during the in-office stress test. In response to the trigger signal, the pacemaker 102 may abort the in-office stress test. FIGS. 12 and 13A–C will now be used to describe an "ambulatory stress test" operating mode of the pacemaker 102 of FIGS. 1–3. The ambulatory stress test operating mode subjects the patient 108 (FIG. 1) to a stress test, during which the pacemaker 102 is used to gradually increase the rate at which the heart 110 (FIG. 1) of the patient 108 beats from a start rate to a stop rate, wherein the stop rate is greater than the start rate. The stress test is intended to be accomplished while the patient 108 is not in a physician's office, and will therefore be referred to as an "ambulatory stress test" herein below.

Figure 12:
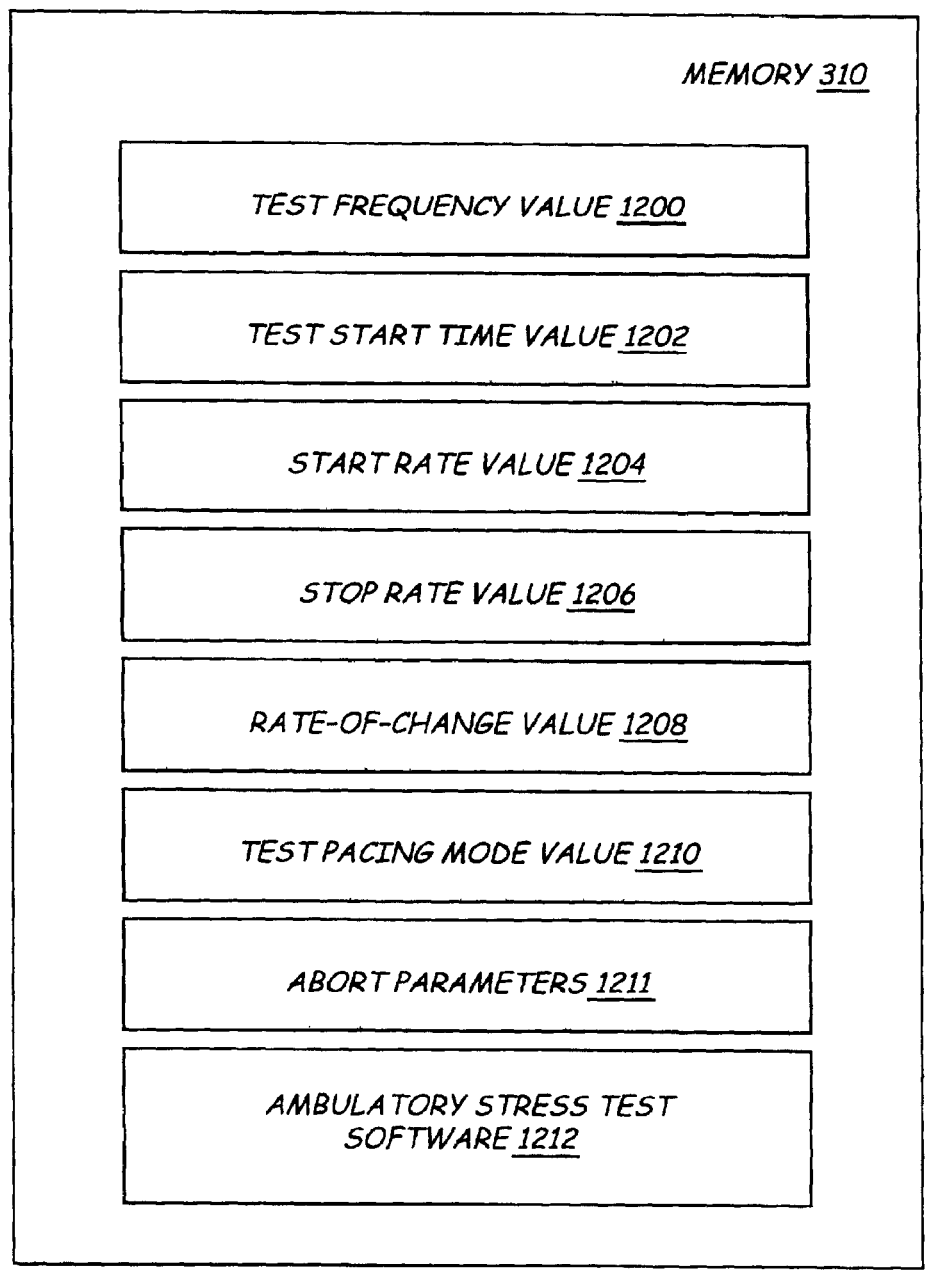
FIG. 12 shows data and instructions stored in the memory of the pacemaker of FIGS. 1–3 and associated with an ambulatory stress test operating mode.

FIG. 12 shows data and instructions stored in the memory 310 (FIG. 3) of the pacemaker 102 and associated with the ambulatory stress test operating mode. In the embodiment of FIG. 12, the memory 310 includes a test frequency value 1200, a test start time value 1202, a start rate value 1204, a stop rate value 1206, a rate-of-change value 1208, a test pacing mode value 1210, abort parameters 1211, and ambulatory stress test software 1212. The test frequency value 1200 specifies a frequency at which the pacemaker 102 is to conduct the ambulatory stress test (e.g., once a day, once a week, etc.) The test start time value 1202 specifies a day of the week and/or a time of day at which the pacemaker 102 is to begin the ambulatory stress test. For example, where the test frequency value 1200 specifies pacemaker 102 is to conduct the ambulatory stress test once a day, the test start time value 1202 may specify the time of day at which the pacemaker 102 is to begin the ambulatory Stress test (e.g., 7 o'clock p.m.). Where the test frequency value 1200 specifies pacemaker 102 is to conduct the ambulatory stress test once a week, the test start time value 1202 may specify both the day of the week and the time of day at which the pacemaker 102 is to begin the ambulatory stress test (e.g., Wednesdays at 7 o'clock p.m.).

The start rate value 1204 specifies a starting pacing rate used by the pacemaker 102 at a beginning of the ambulatory stress test. The stop rate value 1206 specifies a stopping pacing rate used by the pacemaker 102 at an end of the ambulatory stress test. The rate-of-change value 1208 specifies a rate at which the pacemaker 102 increases the heart rate of the patient 108 during the ambulatory stress test. For example, the rate-of-change value 1208 may correspond to "5 beats per minute (bpm)/30 sec.", and may specify that the pacemaker 102 is to increase the heart rate of the patient 108 by 5 beats per minute (bpm) every 30 seconds during the ambulatory stress test.

The test pacing mode value 1210 indicates the pacing mode to be implemented by the pacemaker 102 during the ambulatory stress test (e.g., DDD, AAI, etc.). For example, operating mode value 400 (FIG. 4) may indicate that the pacemaker 102 is to implement a DDD operating mode. During an ambulatory stress test, however, the test pacing mode value 1210 may take priority over the operating mode value 400, and the pacemaker 102 may implement an AAI (atrium only) pacing mode during the ambulatory stress test in accordance with the test pacing mode value 1210.

The abort parameters 1211 indicate values and/or conditions under which the ambulatory stress test is aborted. The abort parameters may include, for example, a maximum allowable ST segment deviation value. In this situation, if the pacemaker 102 detects an ST segment deviation from baseline during the ambulatory stress test that exceeds the maximum allowable ST segment deviation value, the pacemaker 102 may be configured to abort the ambulatory stress test. The abort parameters 1211 may also include a maximum allowable number of premature ventricular contractions (PVCs). In this situation, if the pacemaker 102 detects a number of PVCs during the ambulatory stress test that exceeds the maximum allowable number of PVCs, the pacemaker 102 may be configured to abort the ambulatory stress test.

The abort parameters 1211 may also include a value indicative of how the pacemaker 102 is to respond to the patient activator 118 (FIGS. 1 and 6) during the ambulatory stress test. For example, the patient 108 may be instructed to activate the pushbutton 602 (FIG. 6) of the patient activator 118 during the ambulatory stress test when in distress (e.g., when suffering from a sign of myocardial ischemia). A first activation of the pushbutton 602 by the patient 108 during the ambulatory stress test may result in inclusion of a time stamp marker in the stress test data, and a subsequent second activation of the pushbutton 602 during the ambulatory stress test may cause the pacemaker 102 to abort the ambulatory stress test. The ambulatory stress test software 1212 includes instructions and data used by the CPU 306 (FIG. 3) to implement the ambulatory stress test.

Figure 13A:
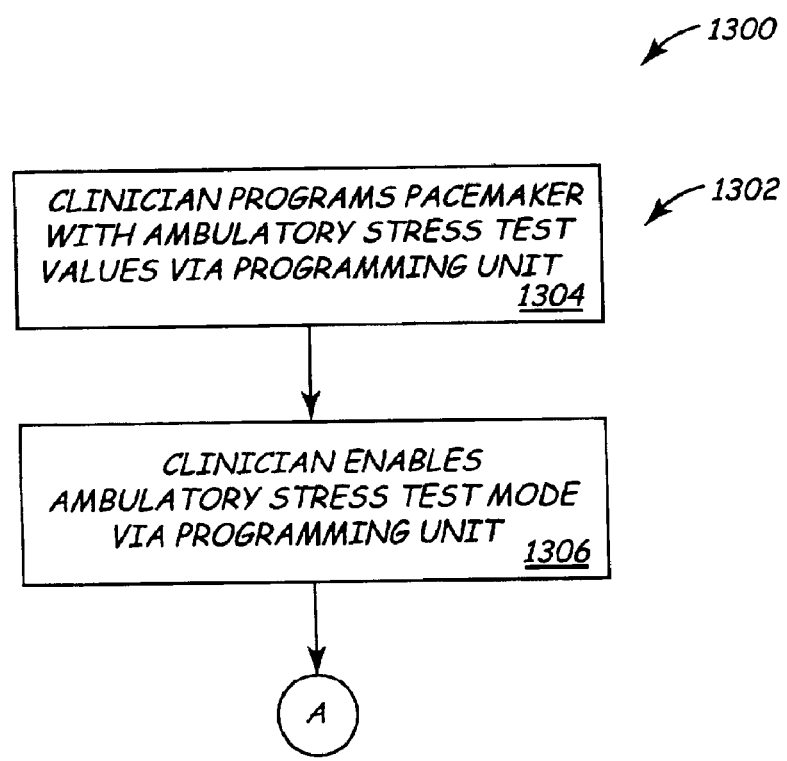
FIGS. 13A–13C in combination form a flow chart illustrating one embodiment of a second method for subjecting the patient of FIG. 1 to a stress test (e.g., an "ambulatory" stress test) using the implantable medical device (IMD) system of FIG. 1.
Figure 13B:
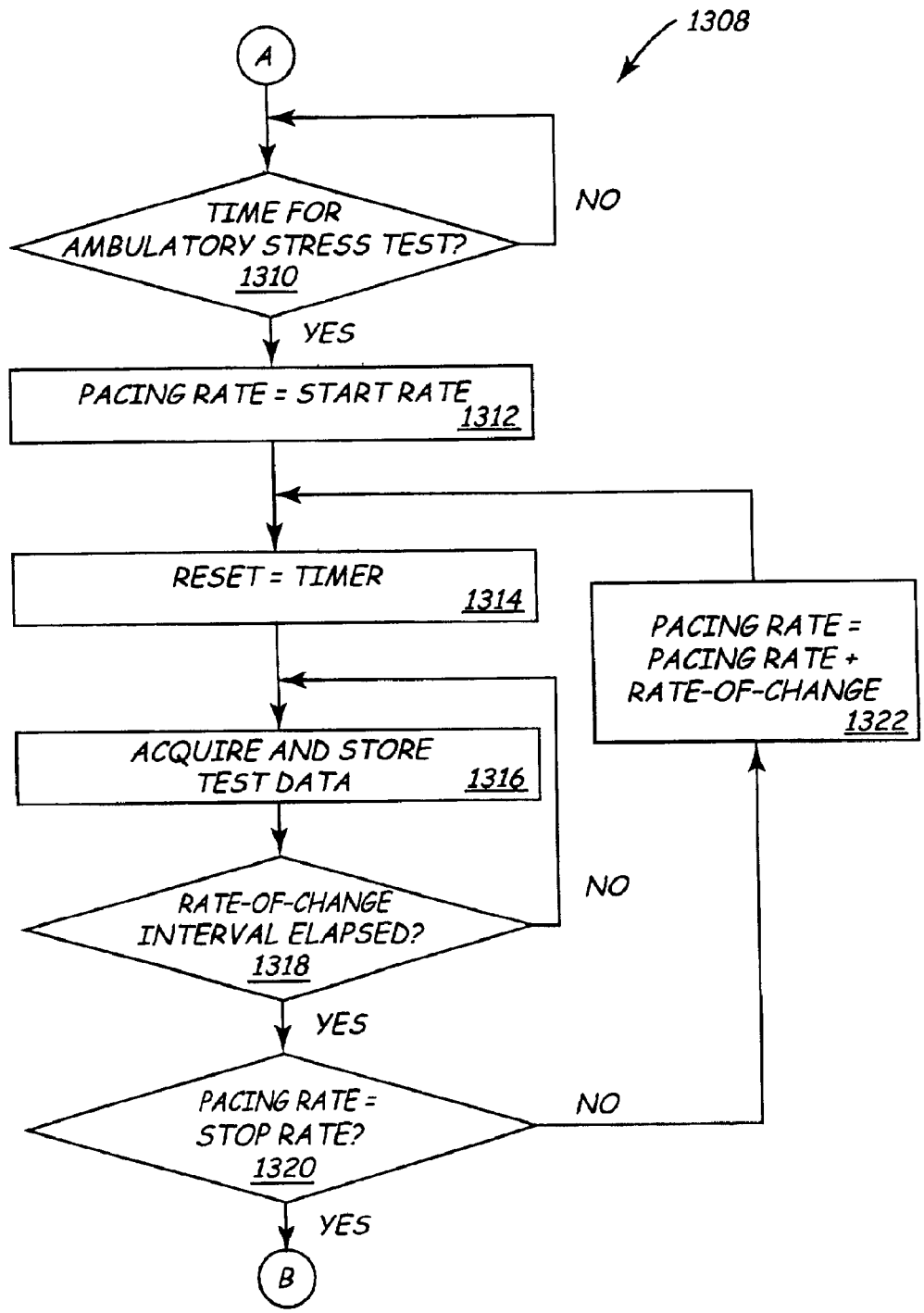
Figure 13C:
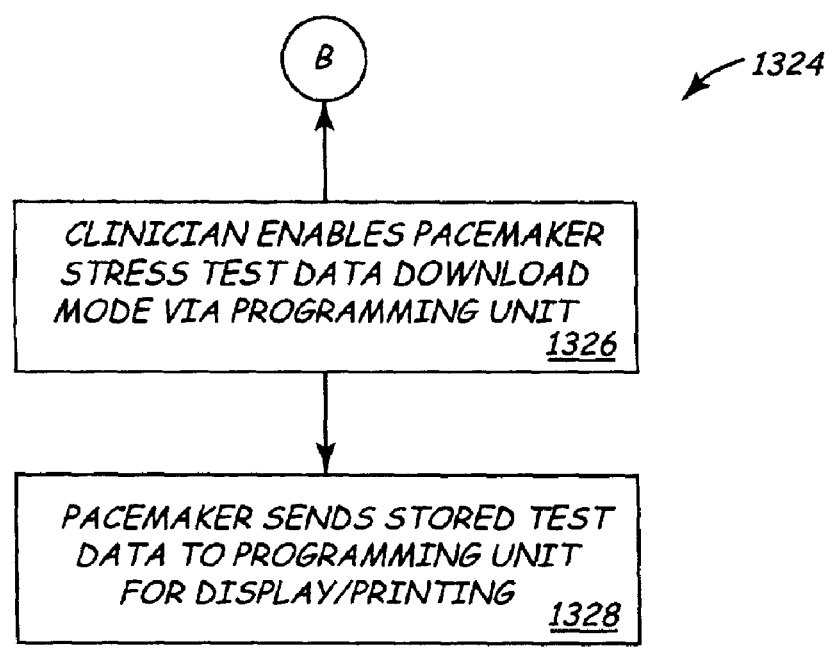

FIGS. 13A–13C in combination form a flow chart illustrating one embodiment of a second method 1300 for subjecting the patient 108 (FIG. 1) to a stress test using the implantable medical device (IMD) system 100 of FIG. 1. Intended to be accomplished while the patient 108 is not in a physician's office, the stress test is referred to as an "ambulatory stress test."

FIG. 13A shows the steps of a first portion 1302 of the method 1300, intended to be performed by a clinician (e.g., in a physician's office). During a step 1304 of the portion 1302, the clinician programs the pacemaker 102 (FIGS. 1 and 2) with ambulatory test values using the programming unit 114 (FIG. 1). Referring back to FIG. 12, the ambulatory test values include the test frequency value 1200, the test start time value 1202, the start rate value 1204, the stop rate value 1206, and the rate-of-change value 1208. During a step 1306 of the portion 1302, the clinician enables the ambulatory test mode of the pacemaker 102 (e.g., by programming the test pacing mode value 1210 via the programming unit 114).

FIG. 13B shows the steps of a second portion 1308 of the method 1300, which may be implemented by the ambulatory stress test software 1212 of FIG. 12. During a step 1310 of the portion 1308, the pacemaker 102 determines if it is time to conduct the ambulatory stress test. For example, the CPU 306 may poll the real time clock circuit 314 (FIG. 3) periodically to determine whether the current day and/or time is equal to the day and/or time specified by the test start time value 1202. Alternately, the CPU 306 may wait for an interrupt signal from the real time clock circuit 314 which indicates the current day and/or time is equal to the day and/or time specified by the test start time value 1202.

When the current day and/or time is equal to the day and/or time specified by the test start time value 1202, the pacemaker 102 accomplishes a step 1312. During the step 1312, the rate at which the pacemaker 102 paces the heart 110 of the patient 108 (FIGS. 1 and 2) is set to the start rate value 1204 (FIG. 12). A timer within the pacemaker 102 (e.g., within the CPU 306, the real time clock circuit 314, or the timing/pacing control unit 304 of FIG. 3) is reset during a step 1314. During a step 1316, the pacemaker 102 acquires and stores stress test data. The stress test data may include, for example, intrathoracic electrogram (EGM) waveform samples produced using the point electrodes 204, 206, and/or 208 shown in FIG. 2. The stress test data may also include intracardiac electrogram (EGM) waveform samples produced using data from electrodes on the atrial lead 104 and/or the ventricular lead 106 (FIGS. 1–2). The stress test data may also include measurements of ST segment deviation as described above, sensor data, pacing threshold data, arrhythmia data, and/or tissue-to-lead impedance data.

The sensor data may include, for example, intracardiac blood pressure and/or oxygen concentration data produced by the blood pressure/oxygen concentration sensing circuits 312 in FIG. 3, respiration rate and/or minute ventilation data produced by the minute ventilation sensing circuit 308 in FIG. 3, and/or activity data produced by the activity sensing circuit 322 in FIG. 3. The pacing threshold data may indicate the amount of electrical energy dissipated by the pacing unit 302 while pacing the heart 110 of the patient 108 (i.e., the amount of electrical energy needed to pace the heart 110 of the patient 108) during the ambulatory stress test, and may be produced by the pacing unit 302. The arrhythmia data may indicate, for example, cardiac arrhythmias sensed by the pacemaker 102 (e.g., atrial/ventricular fibrillation, ventricular tachycardia, premature ventricular contractions, etc.).

As described above, the rate-of-change value 1208 (FIG. 12) specifies a rate at which the pacemaker 102 increases the heart rate of the patient 108 during the ambulatory stress test. The rate-of-change value 1208 conveys both a number of beats per minute (bpm) the heart rate of the patient 108 is to be increased, and a "rate-of-change interval" between heart rate increases. For example, the rate-of-change value 1208 may correspond to "5 beats per minute (bpm)/30 sec.", and thus specify that the pacemaker 102 is to increase the heart rate of the patient 108 by 5 beats per minute (bpm) every 30 seconds during the ambulatory stress test. In this situation, the number of beats per minute (bpm) the heart rate of the patient 108 is to be increased is 5 bpm, and the rate-of-change interval conveyed by the rate-of-change value 1208 is 30 seconds.

While the pacemaker 102 is acquiring and storing stress test data, the pacemaker 102 is also checking the timer to determine whether the rate-of-change interval has elapsed (during a step 1318). For example, the CPU 306 (FIG. 3) may be controlling the acquiring and storing of the stress test data while executing the instructions of the ambulatory stress test software 1212. At the same time, the CPU 306 may be polling the timer periodically to determine whether the rate-of-change interval specified by the rate-of-change value 1208 has elapsed, or waiting for an interrupt signal from the timer which indicates the rate-of-change interval has elapsed.

When the rate-of-change interval has elapsed, the pacemaker 102 checks to see if the current pacing rate is equal to the stop rate value 1206 (during a step 1320). If the current pacing rate is not equal to the stop rate value 1206, the ambulatory stress test is not yet complete. In this situation, the pacing rate is increased during a step 1322, and the steps 1314, 1316, 1318, and 1320 are repeated. During the step 1322, the pacing rate is increased to the current pacing rate plus the number of beats per minute (bpm) specified by the rate-of-change value 1208. If the current pacing rate is equal to the stop rate value 1206 during the step 1320, the second portion 1308 of the ambulatory stress test is complete.

FIG. 13C shows the steps of a third portion 1324 of the method 1300, intended to be performed by a clinician (e.g., in a physician's office, remotely via a communication link, etc.). During a step 1326 of the portion 1324, the clinician enables a stress test download mode of the pacemaker 102 via the programming unit 114 (FIG. 1). In the stress test download mode, the pacemaker 102 sends the stress test data, acquired and stored during the ambulatory stress test, to the programming unit 114 (FIG. 1) for display and/or printing during a step 1328.

Prior to initiating the ambulatory stress test, the pacemaker 102 may be configured to respond to the signal from the patient activator 118 (FIGS. 1 and 6) indicating activation of the pushbutton 602 of the patient activator 118. For example, referring back to FIG. 13B, the pacemaker 102 may be configured to delay step 1312 until the patient 108 activates the pushbutton 602 of the patient activator 118. In this situation, the patient may be allowed to prepare for the ambulatory stress test.

Alternately, the patient 108 may be instructed to activate the pushbutton 602 of the patient activator 118 during the ambulatory stress test when in distress (e.g., when suffering from a sign of myocardial ischemia). A first activation of the pushbutton 602 by the patient 108 during the ambulatory stress test may result in inclusion of a time stamp marker in the stress test data, and a subsequent second activation of the pushbutton 602 during the ambulatory stress test may cause the ambulatory stress test to be aborted.

When an ambulatory stress test is aborted for any reason, a "disable" flag (not shown) may be set in a memory location of the memory 310 (FIG. 3). Subsequent ambulatory stress tests may be blocked until the disable flag is cleared (e.g., by a physician) via the programming unit 114.

The pacemaker 102 may be configured to respond to a trigger signal, produced within the pacemaker 102 and indicating detected myocardial ischemia within the patient 108 during the ambulatory stress test, by aborting the stress test. For example, the pacemaker 102 may include myocardial ischemia detection software stored in the memory 310 (see FIG. 14). The myocardial ischemia detection software may be executed by the CPU 306 (FIG. 3) during the ambulatory test, and the myocardial ischemia detection software may produce a trigger signal when myocardial ischemia is detected in the patient 108 during the ambulatory stress test. The myocardial ischemia detection software may use the abort parameters 1211 (FIG. 12) in order to detect myocardial ischemia in the patient 108, and/or to generate the trigger signal. In response to the trigger signal, the pacemaker 102 may abort the ambulatory stress test, and may also set the disable flag (not shown) in the memory 310 (FIG. 3) as described above.

For example, the myocardial ischemia detection software may implement an ST segment deviation detection algorithm as described above. In this situation, the myocardial ischemia detection software may insert time stamp markers into the stress test data when minor ST segment abnormalities are detected, and may abort the ambulatory stress test if a major ST segment abnormality is detected.

Referring back to FIG. 13B, in order to avoid an abrupt change in the heart rate of the patient 108 at the beginning of the ambulatory stress test, the pacemaker 102 may check to make sure a current heart rate of the patient 108 does not differ substantially from the start rate value 1206 (FIG. 12) prior to pacing the heart 110 of the patient 108 at the start rate value 11206 during the step 1312. For example, if the current heart rate of the patient 108 prior to the step 1312 is substantially greater than the start rate value 1206, the step 1312 may be delayed until the current heart rate of the patient 108 slows and falls below the start rate value 1000 for a period of time (e.g., 30 seconds).

After the heart 110 of the patient 108 has been paced by the pacemaker 102 at the maximum rate indicated by the stop rate value 1206 for an entire rate-of-change interval, the pacing rate is decreased linearly or monotonically over a period of time from the maximum rate indicated by the stop rate value 1206 to the rate indicated by the start rate value 1204. For example, a second rate-of-change value (not shown) stored within the memory 310 (FIG. 3) may specify a rate at which the pacemaker 102 is to decrease the heart rate of the patient 108 during a final portion of the ambulatory stress test. The second rate-of-change value may convey both a number of beats per minute (bpm) the heart rate of the patient 108 is to be decreased, and a "rate-of-change interval" between heart rate decreases. For example, the second rate-of-change value may correspond to "30 beats per minute (bpm)/60 sec.", and thus specify that the pacemaker 102 is to decrease the heart rate of the patient 108 by 30 beats per minute (bpm) every 60 seconds during the final portion of the ambulatory stress test.

Figure 14:
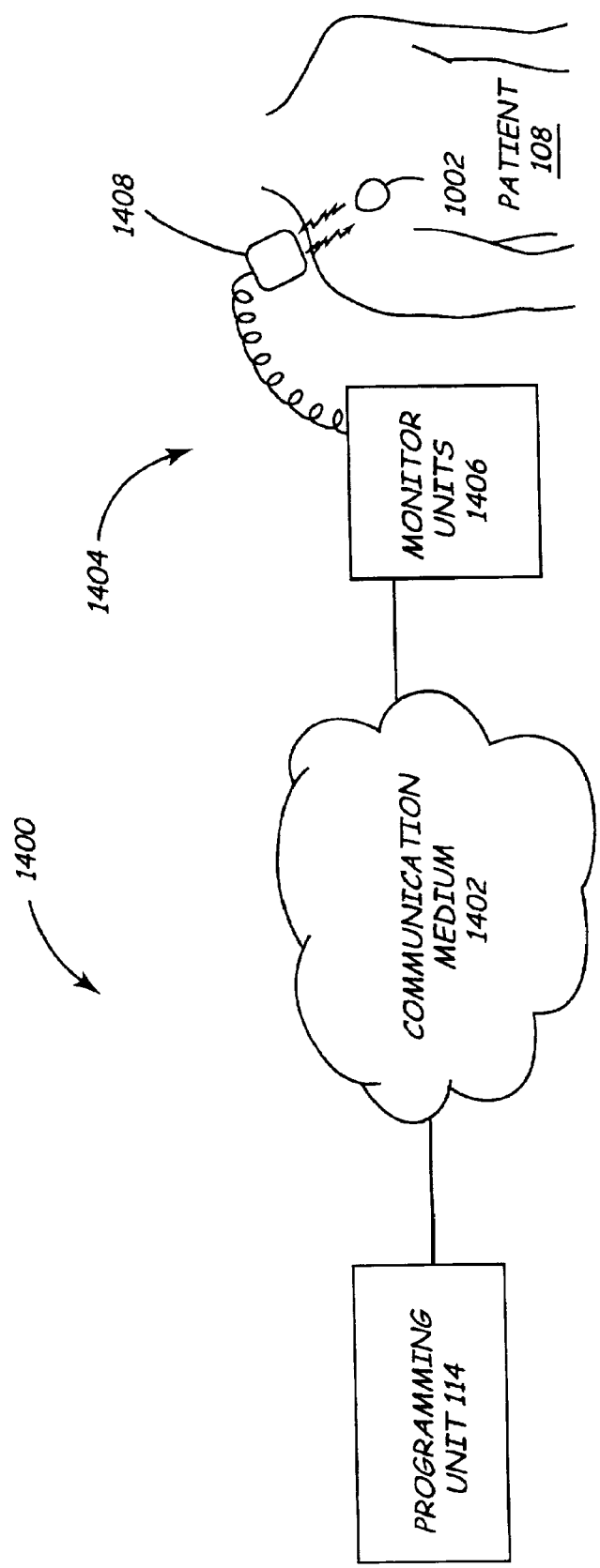
FIG. 14 is a diagram of one embodiment of a system for accomplishing an ambulatory stress test via a communication medium (e.g., a telephone network)

FIG. 14 is a diagram of one embodiment of a system 1400 for accomplishing an ambulatory stress test via a communication medium 1402. In FIG. 14, the patient 108 is located remote from the programming unit 114, which is typically in a physician's office. A monitor system 1404, positioned proximate the patient 108, is coupled to the programming unit 114 via the communication medium 1402 (e.g., a wired/wireless network such as a telephone network). The monitor system 1404 includes a monitor unit 1406 coupled to the programming unit 114 via the communication medium 1402, and a monitor head 1408 connected to the monitor unit 1406.

In order to initiate an ambulatory stress test using the system 1400, the patient 108 may establish a communication link between the monitor unit 1406 and the programming unit 114. For example, the communication medium 1402 may be a telephone network, and the patient 108 may establish a telephone connection between the monitor unit 1406 and the programming unit 114 (e.g., by using the monitor unit to dial a telephone number associated with the programming unit 114). The patient 108 then positions the monitor head 1408 proximate the pacemaker 102 as shown in FIG. 14. During the ambulatory stress test, the monitor head 1408 is in wireless communication (e.g., radio frequency communication) with the pacemaker 102. A physician operating the programming unit 114 may then initiate the ambulatory stress test described above (e.g., the ambulatory stress test of FIGS. 13A–C) via the communication link. During the ambulatory stress test (e.g., during the step 1328 of FIG. 13C), the pacemaker 102 transmits stress test data to the monitor unit 1406 via the monitor head 1408, and the monitor unit 1408 conveys the stress test data to the programming unit 114 via the communication medium 1402. The programming unit 114 may display the stress test data on a display screen (see FIG. 17), and the physician may view the displayed stress test data.

Figure 15:
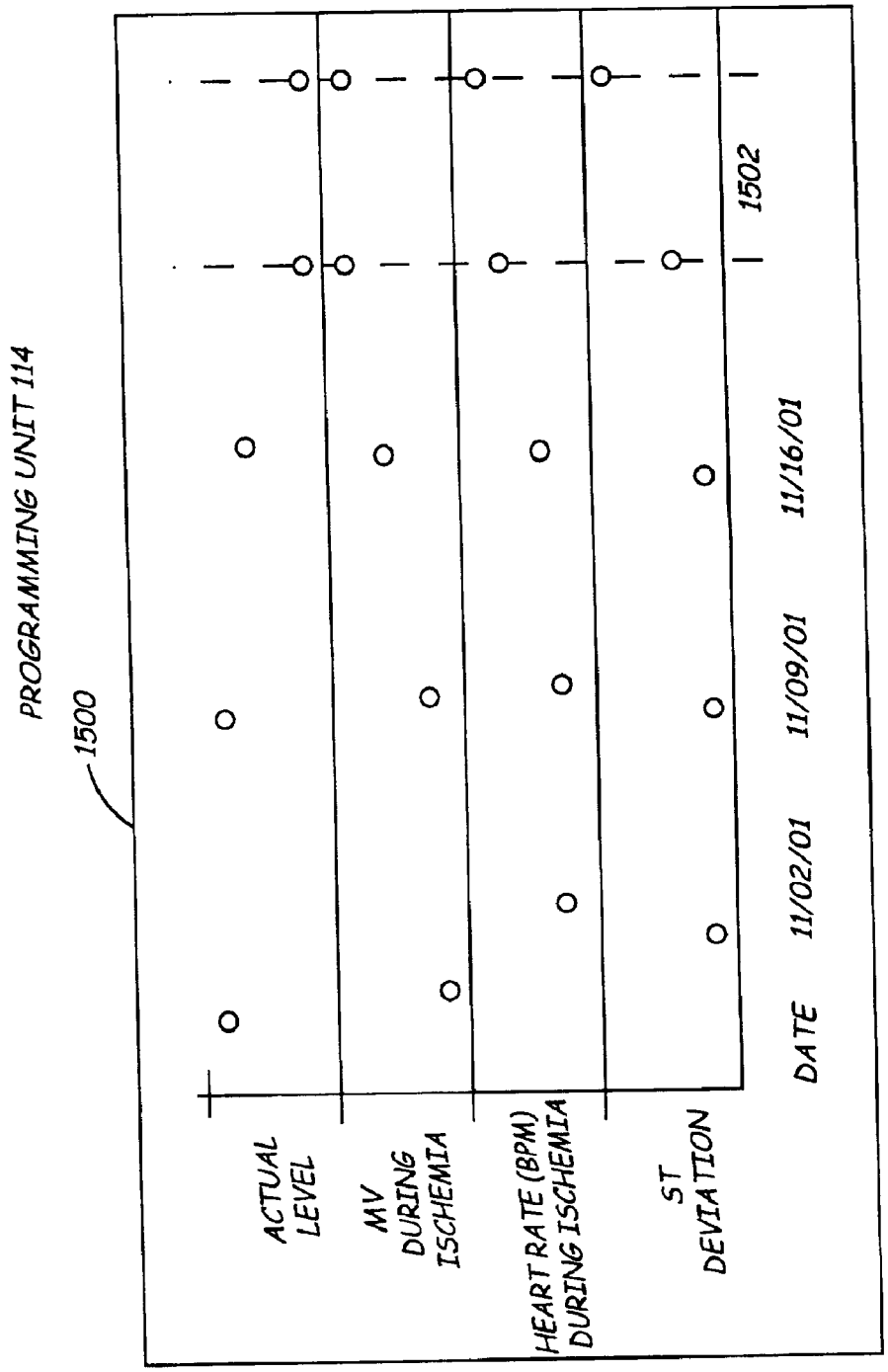
FIG. 15 illustrates an exemplary graph of data obtained from the pacemaker of FIGS. 1–3 and displayed on a display screen of the programming unit of FIG. 1.

FIG. 15 illustrates an exemplary graph of data obtained from the pacemaker 102 of FIGS. 1–3 and displayed on a display screen 1500 of the programming unit 114 of FIG. 1. The graph includes an "activity level" vertical axis, wherein the plotted activity level values represent activity levels of the patient 108 (FIG. 1) during the ambulatory stress tests. The graph also includes a "minute ventilation (MV) level during ischemia" vertical axis, wherein the plotted minute ventilation (MV) level during ischemia values represent minute ventilation (MV) levels of the patient 108 when myocardial ischemia was detected within the patient 108 during the ambulatory stress tests. The graph also includes a "heart rate (bpm) during ischemia" vertical axis, wherein the plotted heart rate (bpm) during ischemia values represent heart rates of the patient 108 in beats per minute (bpm) when myocardial ischemia was detected within the patient 108 during the ambulatory stress tests. The graph also includes an "ST deviation" vertical axis, wherein the plotted ST deviation values represent deviations of ST segments of electrogram (EGM) waveforms of the patient 108 during the ambulatory stress tests.

In the embodiment of FIG. 15, dashed vertical lines are used to denote data sets resulting from patient activation of the pushbutton 602 (FIG. 6) of the patient activator 118 (FIGS. 1 and 6) when suffering from signs of myocardial ischemia. For example, in FIG. 15, the first 3 data sets, plotted vertically, are stress test data sets resulting from scheduled ambulatory stress tests. The last 2 data sets, denoted by dashed vertical lines 1502, are data sets resulting from data stored within the pacemaker 102 (FIGS. 1–2) when the patient 108 activated the pushbutton 602 (FIG. 6) of the patient activator 118 (FIGS. 1 and 6) when suffering from signs of myocardial ischemia.

It is noted that the data of FIG. 15 may be used to track a progression of myocardial ischemia over time at regular intervals. Such information is believed to be very valuable in the treating myocardial ischemia.

Figure 16:
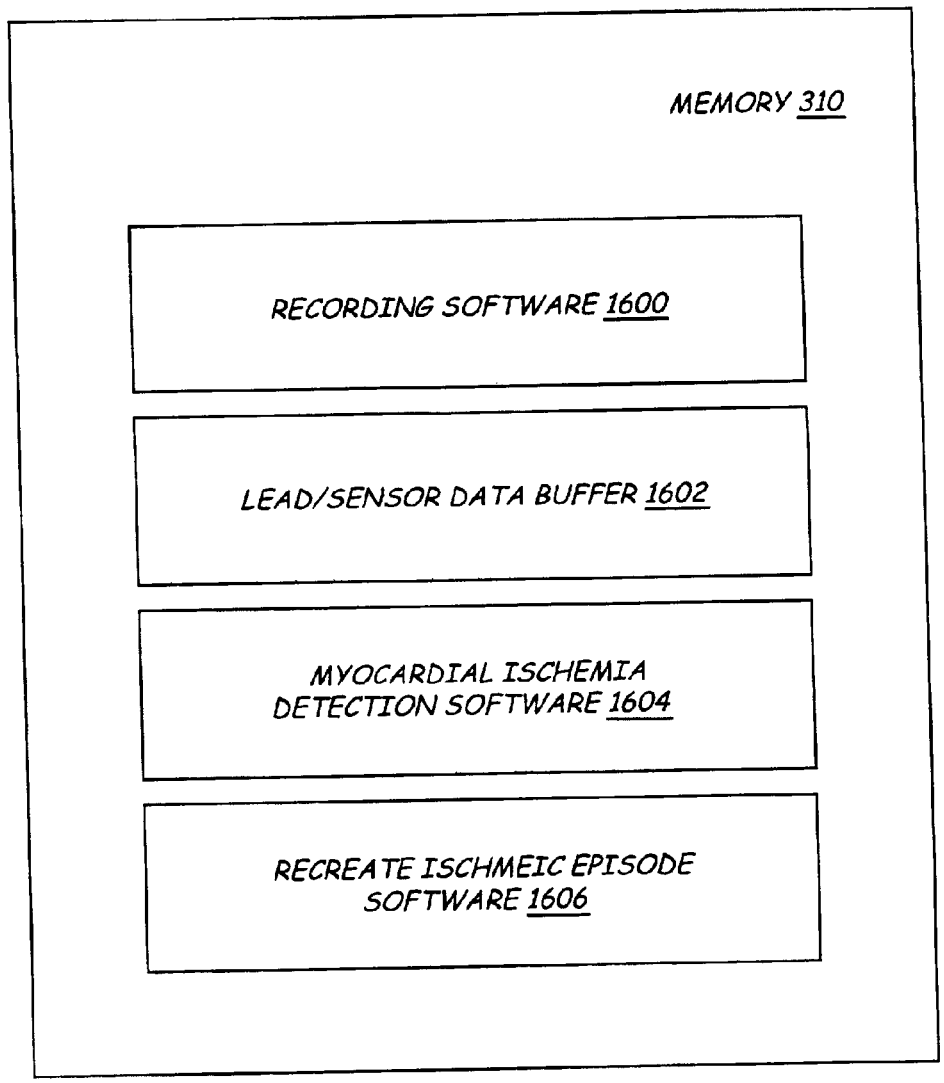
FIG. 16 shows data and instructions stored in the memory of the pacemaker of FIGS. 1–3 and associated with "record ischemic episode" mode and a "recreate ischemic episode" mode of the pacemaker.
Figure 17:
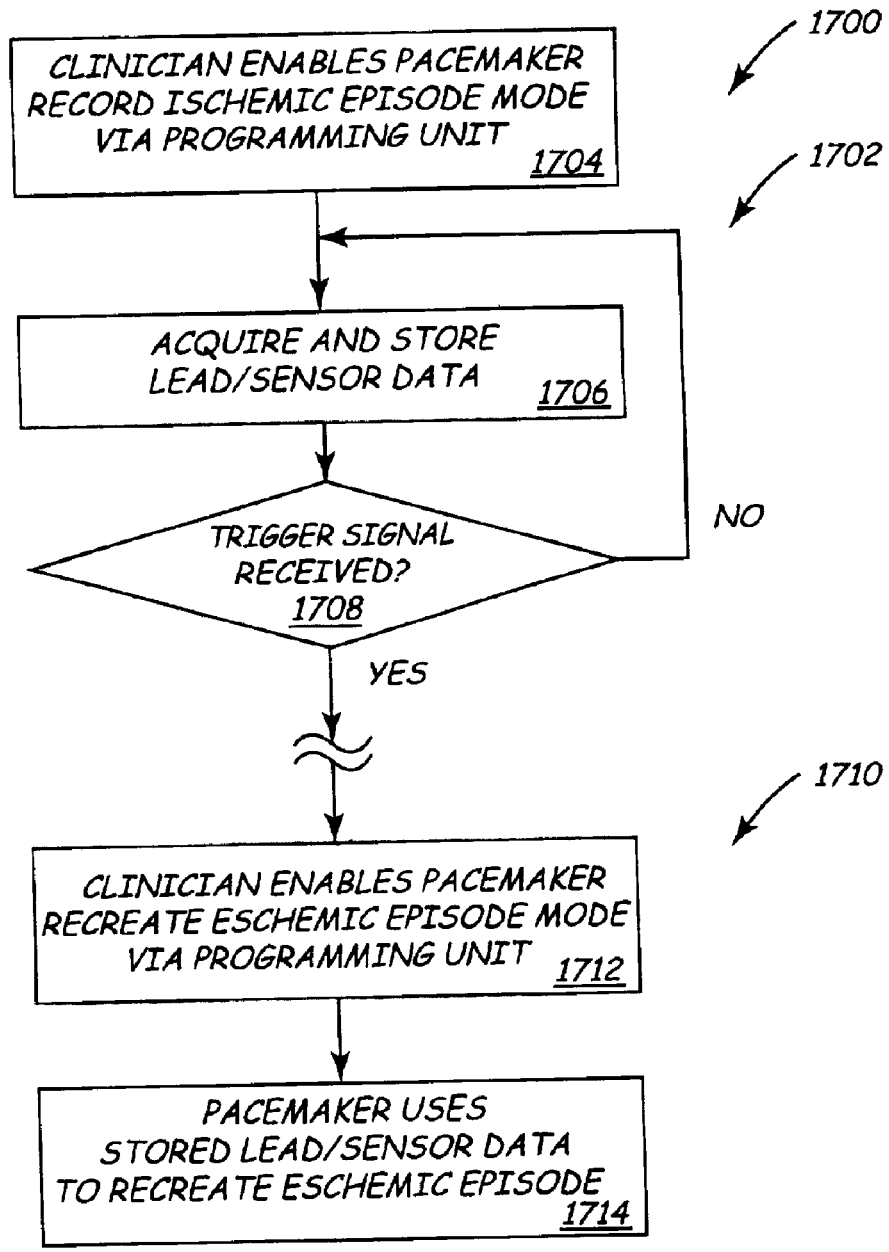
FIG. 17 is a flow chart illustrating a method for recording cardiac conditions existing within the patient of FIG. 1 during an episode of myocardial ischemia, and subsequently recreating the cardiac conditions existing in the patient during the episode of myocardial ischemia.

FIGS. 16 and 17 will now be used to describe a "record ischemic episode" operating mode and a "recreate ischemic episode" operating mode of the pacemaker 102 of FIGS. 1–3. While in the record ischemic episode operating mode, the pacemaker 102 continuously acquires lead/sensor data and stores the lead/sensor data in a buffer (e.g., a circular buffer). The pacemaker 102 also monitors the lead/sensor data for signs of myocardial ischemia within the patient 108.

When the pacemaker 102 detects myocardial ischemia within the patient 108, the pacemaker 102 stops storing lead/sensor data in the circular buffer. The pacemaker 102 may then be programmed (e.g., while the patient 108 is in a physician's office) to use the stored ischemic episode data to recreate the cardiac conditions associated with the ischemic episode.

FIG. 16 shows data and instructions stored in the memory 310 (FIG. 3) of the pacemaker 102 and associated with the record ischemic episode and the recreate ischemic episode operating modes. In the embodiment of FIG. 16, the memory 310 includes recording software 1600, a lead/sensor data buffer 1602, myocardial ischemia detection software 1604, and recreate ischemic episode software 1606. The recording software 1600 includes instructions and data for acquiring lead/sensor data, and storing the lead/sensor data in the lead/sensor data buffer 1602. In general, the lead/sensor data buffer 1602 is large enough to store enough lead/sensor data to recreate an episode of myocardial ischemia (i.e., an ischemic episode) experienced by the patient 108. The lead/sensor data buffer 1602 may also be used to store additional lead/sensor data associated with the ischemic episode. When the lead/sensor data buffer 1602 becomes fill, the recording software 1600 stores lead/sensor data in the lead/sensor data buffer 1602 such that the newest lead/sensor data overwrites the oldest lead/sensor data stored in the lead/sensor data buffer 1602. In other words, the recording software 1600 manages the lead/sensor data buffer 1602 as a circular buffer.

In general, the CPU 306 (FIG. 3) executes instructions of the recording software 1600 and the myocardial ischemia detection software 1604 while the pacemaker 102 is in the record ischemic episode operating mode. The instructions of the recording software 1600 cause the CPU 306 to store lead/sensor data in the lead/sensor data buffer 1602, and the instructions of the myocardial ischemia detection software 1604 cause the CPU 306 (FIG. 3) to analyze lead/sensor data to determine if the patient 108 is experiencing an ischemic episode. When the CPU 306 detects myocardial ischemia within the patient 108 (via the instructions of the myocardial ischemia detection software 1604), the CPU 306 stops storing lead/sensor data in the lead/sensor data buffer 1602.

Specifically, the instructions of the myocardial ischemia detection software 1604 cause the CPU 306 (FIG. 3) to analyze samples of electrogram (EGM) waveforms. The electrogram (EGM) waveforms may include intrathoracic electrogram (EGM) waveforms produced using the point electrodes 204, 206, and/or 208 of FIG. 2. Alternately, or in addition, the electrogram (EGM) waveforms may include intracardiac electrogram (EGM) waveforms produced using the electrodes on the atrial lead 104 and/or the ventricular lead 106 (FIGS. 1–2).

In causing the CPU 306 to analyze the electrogram (EGM) waveform samples, the myocardial ischemia detection software 1604 may implement an ST segment analysis algorithm to determine ST segment deviation. (See, for example, U.S. Pat. No. 6,128,526). As described above, the points on the electrogram (EGM) waveform labeled 1, 2, 3, and 4 in FIGS. 8 and 9 indicate waveform sampling points for the ST segment analysis algorithm. The R-wave peak may be used as a time reference point (i.e., a fiducial point). When an R-wave peak is detected, the sample points 1, 2, 3, and 4 may be determined relative to the R-wave peak. The amplitude of the electrogram (EGM) waveform at sample point 1, preceding the QRS complex, may be used to establish an isoelectric or baseline level of the electrogram (EGM) waveform. Disparities between amplitudes of the electrogram (EGM) waveforms produced by the multiple differential sense amplifiers at sample points 1, 2, 3, and 4 may be used to detect ST segment deviation (e.g., ST segment deviation or depression), wherein such ST segment deviation is indicative of an episode of myocardial ischemia within the patient 108 (FIG. 1).

The myocardial ischemia detection software 1604 may also cause the CPU 306 to analyze electrogram (EGM) waveform samples (e.g., produced using data from electrodes on the atrial lead 104 and/or the ventricular lead 106 shown in FIGS. 1 and 2) to determine an onset of myocardial ischemia within the patient 108. The myocardial ischemia detection software 1604 may also cause the CPU 306 to analyze intracardiac blood pressure and/or oxygen concentration data produced by the blood pressure/oxygen concentration sensing circuits 312 in FIG. 3, respiration rate data produced by the minute ventilation sensing circuit 308 in FIG. 3, minute ventilation (MV) data produced by the minute ventilation (MV) sensing circuit 308 in FIG. 3, and/or activity data produced by the activity sensing circuit 322 in FIG. 3, to determine an onset of myocardial ischemia within the patient 108.

In addition, the myocardial ischemia detection software 1604 may also cause the CPU 306 to stop storing lead/sensor data in the lead/sensor data buffer 1602 in response to a signal from the patient activator 118 (FIGS. 1 and 6) indicating activation of a pushbutton of the patient activator (e.g., the pushbutton 602 of FIG. 6). The patient 108 may press the pushbutton 602 of the patient activator 118 when in distress (e.g., when suffering from a sign of myocardial ischemia).

It is noted that the pacemaker 102 may be configured to store sensor data in the memory 310 (FIG. 3) until the trigger signal is received, and to continue to store sensor data in the memory 310 for a predetermined amount of time after the trigger signal is received.

FIG. 17 is a flow chart illustrating a method 1700 for recording cardiac conditions existing within the patient 108 (FIG. 1) during an episode of myocardial ischemia, and subsequently recreating the cardiac conditions existing in the patient 108 during the episode of myocardial ischemia. The method 1700 employs the implantable medical device (IMD) system 100 of FIG. 1. A first portion 1702 of the method 1700 is associated with the record ischemic episode mode of the pacemaker 102. During a step 1704 of the portion 1702, the clinician enables the record ischemic episode mode of the pacemaker 102 via the programming unit 114. The pacemaker 102 acquires and stores lead/sensor data in the lead/sensor data buffer 1602 (FIG. 16) during a step 1706. While acquiring and storing lead/sensor data, the pacemaker 102 is configured to receive a trigger signal indicating detection of an ischemic episode within the patient 118 (during a step 1708). The trigger signal may be generated, for example, by the myocardial ischemia detection software 1604 (FIG. 16) when the CPU 306 is to stop storing lead/sensor data in the lead/sensor data buffer 1602. When the trigger signal is generated, the pacemaker 102 stops storing lead/sensor data in the lead/sensor data buffer 1602.

A second portion 1710 of the method 1700 is associated with the recreate ischemic episode mode of the pacemaker 102. During a step 1712 of the second portion 1710, the clinician enables the recreate ischemic episode mode of the pacemaker 102 via the programming unit 114. During a step 1714, the pacemaker 102 uses the lead/sensor data stored in the lead/sensor data buffer 1602 to simulate (e.g., recreate) the cardiac conditions existing in the patient 108 (FIG. 1) during the previous episode of myocardial ischemia.

During the second portion 1710 of the method 1700, the rate at which the pacemaker 102 paces the heart 110 of the patient 108 may be increased and/or decreased linearly or monotonically over periods of time to prevent abrupt changes in heart rate. For example, the lead/sensor data stored in the lead/sensor data buffer 1602 may indicate an "ischemic" heart rate of the patient 108, occurring during the recorded ischemic episode, was substantially greater than a current heart rate of the patient 108. In this situation, a first rate-of-change value (not shown) stored within the memory 310 (FIG. 3) may specify a rate at which the pacemaker 102 is to increase the heart rate of the patient 108 from the current heart rate to the ischemic heart rate when the pacemaker 102 initially enters the recreate ischemic episode mode. A second rate-of-change value (not shown) stored within the memory 310 (FIG. 3) may specify a rate at which the pacemaker 102 is to decrease the heart rate of the patient 108 from the ischemic heart rate to the current heart rate after the ischemic episode has been recreated. The first and second rate-of-change values may convey both a number of beats per minute (bpm) the heart rate of the patient 108 is to be increased and decreased, respectively, and "rate-of-change intervals" between heart rate increases and decreases as described above.

Figure 18:
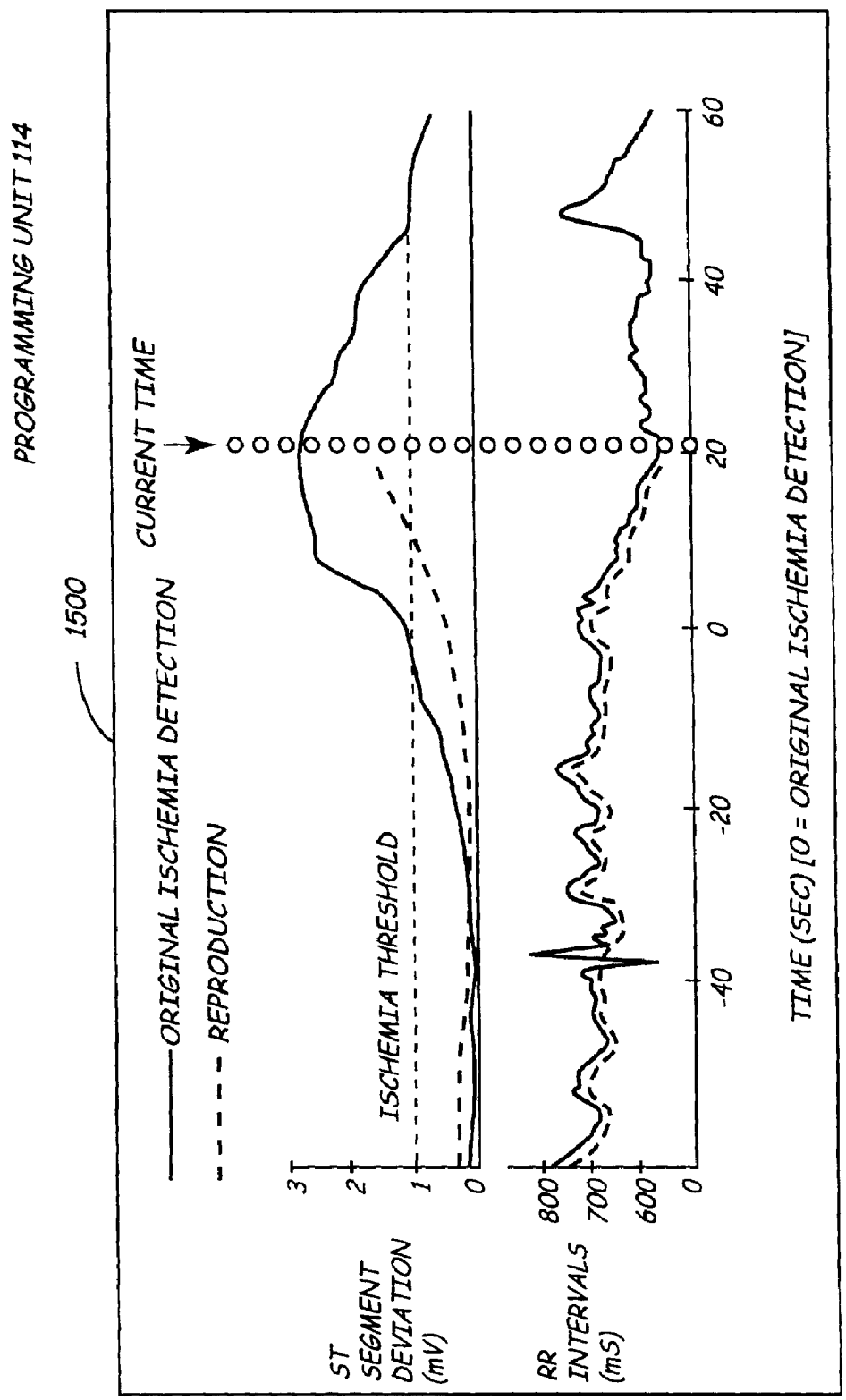
FIG. 18 is an exemplary graph of data generated during recreation of an ischemic episode being displayed on the display screen of the programming unit (see FIGS. 1 and 15), wherein data generated during the recreation of the ischemic episode is displayed on top of data obtained during the ischemic episode.

FIG. 18 is an exemplary graph of data generated during recreation of an ischemic episode being displayed on the display screen 1500 (see FIG. 15) of the programming unit 114 (see FIGS. 1 and 15). In FIG. 18, the data generated during the recreation of the ischemic episode is displayed on top of the data obtained during the ischemic episode. The data obtained during the ischemic episode may have been recorded when the pacemaker 102 was in the record ischemic episode mode, and in response to a trigger signal as described above with respect to the first portion 1702 of the method 1700 of FIG. 17. As indicated in FIG. 18, the pacemaker 102 may store sensor data in the memory 310 (FIG. 3) until the trigger signal is received, and may continue to store sensor data in the memory 310 for a predetermined amount of time after the trigger signal is received.

In FIG. 18, a dotted vertical line marks a current time during the recreation of the ischemic episode, and moves across the display screen 1500 from right to left as time progresses during the recreation of the ischemic episode. It is noted that the data obtained during the ischemic episode may have been acquired in response to activation of the pushbutton 602 (FIG. 6) of the patient activator 118 (FIGS. 1 and 6) by the patient 108 (FIG. 1) as described above.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. An implantable medical device (IMD) for implantation in a patient to detect symptomatic and asymptomatic myocardial ischemia, comprising:

pacing circuitry configured to selectively produce pacing pulses at a programmable pacing rate for delivery to muscle tissue of a heart of the patient, wherein the pacing circuitry is configurable to subject the patient to a variety of stress tests, and wherein the variety of stress tests further comprise:

(i) a first stress test protocol wherein the programmable pacing rate is slowly increased at from between about five paces per minute (ppm) to about ten ppm from a start rate to a stop rate, wherein the stop rate is greater than the start rate, and the patient's response to the first stress test protocol is acquired and stored in a memory structure as a part of a stress test data set;

(ii) a second stress test protocol wherein the IMD is configurable to store timing information specifying a time the IMD is to subject the patient to the first stress test protocol, and to subject the patient to the first stress test protocol at the time, day and/or date specified by the timing information, and the patient's response to the second stress test protocol is acquired and stored in the memory structure as a part of the stress test data set; and (iii) a third stress test protocol wherein the protocol comprises recreating the physiologic conditions of a previously stored episode of paced or intrinsic symptomatic myocardial ischemia that were stored in the memory structure after the patient triggers an episode storage event, and the patient's response to the third stress test protocol is acquired and stored in the memory structure as a part of the stress test data set.

2. The implantable medical device (IMD) as recited in claim 1, wherein the timing information specifies a frequency and a time of day the IMD is to subject the patient to the stress test.

3. The implantable medical device (IMD) as recited in claim 1, wherein the IMD is adapted to receive a signal, and configurable to subject the patient to at least one of the first, second and third stress test protocol in response to the signal.

4. The implantable medical device (IMD) as recited in claim 3, wherein the signal is a radio frequency signal.

5. The implantable medical device (IMD) as recited in claim 1, wherein the IMD is configurable to detect at least one sign of myocardial ischemia within the patient during the first, second and third stress test protocols, and wherein the IMD is configurable to abort each the stress test protocols when the at least one sign of myocardial ischemia is detected within the patient.

6. The implantable medical device (IMD) as incited in claim 5, wherein the at least one sign of myocardial ischemia comprises deviation of an ST segment of an electrogram (EGM) waveform from an isoelectric baseline of the electrogram (EGM) waveform.

7. The implantable medical device (IMD) as recited in claim 1, wherein the IMD is adapted to receive a signal, and configurable to abort at least one of the first, second and third stress test protocols in progress at a time the signal is received.

8. The implantable medical device (IMD) as recited in claim 7, wherein the signal is a radio frequency signal.

9. The implantable medical device (IMD) as recited in claim 1, wherein during at least the first stress test protocol, the pacing rate is monotonically increased from the start rate to the stop rate.

10. The implantable medical device (IMD) as recited in claim 1, wherein during at least the first stress test protocol, the pacing rate is increased from the start rate to the stop rate by: (i) programming the pacing rate to be the start rate, and (ii) at pre-selected time intervals, reprogramming the pacing rate to be a sum of a current value of the pacing rate and a pre-selected rate-of-change value.

11. The implantable medical device (IMD) as recited in claim 1, wherein the stress test data set comprises electrogram (EGM) waveform data produced within the IMD.

12. The implantable medical device (IMD) as recited in claim 11, wherein the IMD is coupled to receive a signal from at least one intrathoracic electrode, and wherein the electrogram (EGM) waveform is an intrathoracic electrogram (EGM) waveform.

13. The implantable medical device (IMD) as recited in claim 11, wherein the IMD is coupled to receive a signal generated within the heart, and wherein the electrogram (EGM) waveform is an intracardiac electrogram (EGM) waveform.

14. The implantable medical device (IMD) as recited in claim 11, wherein the electrogram (EGM) waveform comprises an ST segment and an isoelectric baseline, and wherein the EGM data comprises a measurement of deviation of the ST segment from the isoelectric baseline.

15. The implantable medical device (IMD) as recited in claim 1, wherein the IMD is coupled to receive sensor data, and wherein the stress test data set comprises the sensor data.

16. The implantable medical device (IMD) as recited in claim 1, wherein the stress test data set comprises pacing threshold data produced within the IMD and indicative of an amount of energy dissipated by the pacing circuitry while producing the pacing pulses.

17. The implantable medical device (IMD) as recited in claim 1, wherein the stress test data set comprises arrhythmia data produced within the IMD and indicative of detected arrhythmias of the heart of the patient.

18. The implantable medical device (IMD) as recited in claim 1, wherein the IMD is coupled to receive a first intrinsic depolarization signal and a second intrinsic depolarization signal from the heart of the patient, and wherein the IMD is configurable to operate in a demand mode, and wherein in the demand mode, if the second intrinsic depolarization signal is not received within a predetermined time period, determined by the pacing rate, after the first intrinsic depolarization signal is received, the pacing circuitry is signaled to produce one of the pacing pulses.

19. The implantable medical device (IMD) as recited in claim 1, wherein during an initial portion of one of the first stress test protocol and the second stress test protocol: (i) the programmed pacing rate is programmed such that the pacing rate is increased from a start rate to a stop rate, and (ii) stress test data set is acquired and stored within the IMD, and wherein during a final portion of one of the first stress test protocol and the second stress test protocol the pacing rate is programmed such that the programmed pacing rate is decreased from the stop rate to the start rate, and the IMD provides the stress test data stored within the IMD.

20. The implantable medical device (IMD) as recited in claim 1, wherein the IMD is a pacemaker.

21. The implantable medical device (IMD) as recited in claim 1, wherein pacing pulses received by the muscle tissue of the heart cause the muscle tissue to depolarize.

22. An implantable medical device for implantation in a patient, comprising;
    pacing circuitry configured to selectively produce pacing pulses at a programmable pacing rate for delivery to muscle tissue of a heart of the patient;
    a memory for storing data, including a stress test data set; and
    a control unit coupled to the pacing circuitry and the memory, wherein the control unit is configurable to subject the patient to a variety of stress test protocols, and wherein:
    during a first the stress test protocol the control unit programs the pacing rate such that the pacing rate is increased incrementally at about between five paces per minute and ten ppm from a start rate to a stop rate, wherein the stop rate is greater than the start while acquiring and storing the stress test data set in the memory; and
    during a second stress test protocol the control unit recreates the physiologic conditions of a previously stored episode of paced or intrinsic symptomatic myocardial ischemia that were stored in the memory after the patient triggers an episode storage event, and the patient's response to the third stress test protocol is acquired and stored in the memory as a part of the stress test data set, wherein the device further comprises:
    a clock circuit coupled to the control unit and configured to keep track of time; and
    a telemetry unit coupled to the control unit and configured to send and receive signals and data; and
    wherein the control unit is configurable to receive timing data or a trigger signal via the telemetry unit, wherein the timing data specifies a time the IMD is to subject the patient to the stress test so that the clock circuit or the trigger signal to subject the patient to one of the first stress test protocol and the second stress test protocol at the time specified by the timing data or upon receipt of the trigger signal, respectively.

23. The implantable medical device (IMD) as recited in claim 22, wherein the timing data specifies a frequency and a time of day the IMD is to subject the patient to the stress test.

24. The implantable medical device (IMD) as recited in claim 22, further comprising a telemetry unit coupled to the control unit and configured to send and receive signals and data, wherein the control unit is configurable to subject the patient to one of the variety of stress test protocols in response to a signal received via the telemetry unit.

25. The implantable medical device (IMD) as recited in claim 24, wherein the signal is a radio frequency signal.

26. The implantable medical device (IMD) as recited in claim 22, wherein the control unit is configurable to detect at least one sign of myocardial ischemia within the patient during one of the variety of stress test protocols, and wherein the control unit is configurable to abort and applied one of the variety of stress test protocols when the at least one sign of myocardial ischemia is detected within the patient.

27. The implantable medical device (IMD) as recited in claim 26, wherein the at least one sign of myocardial ischemia comprises deviation of an ST segment of an electrogram (EGM) waveform from an isoelectric baseline of the electrogram (EGM) waveform.

28. The implantable medical device (IMD) as recited in claim 22, further comprising a telemetry unit coupled to the control unit and configured to send and receive signals and data, wherein the control unit is configurable to abort a stress test in progress at a time a signal is received via the telemetry unit.

29. The implantable medical device (IMD) as recited in claim 28, wherein the signal is a radio frequency signal.

30. The implantable medical device (IMD) as recited in claim 22, wherein during the stress test, the control unit programs the pacing rate such that the pacing rate is monotonically increased from the start rate to the stop rate.

31. The implantable medical device (IMD) as recited in claim 22, wherein during the stress test, the control unit (i) programs the pacing rate to be the start rate, and (ii) at pre-selected time intervals, reprograms the pacing rate to be a sum of a current value of the pacing rate and a pre-selected rate-of-change value.

32. The implantable medical device (IMD) as recited in claim 22, further comprising electrode sensing circuitry coupled to receive electrode signals and configured to produce electrogram (EGM) waveform data derived from an electrogram (EGM) waveform, wherein the stress test data set comprises the electrogram (EGM) waveform data.

33. The implantable medical device (IMD) as recited in claim 32, wherein the electrode sensing circuitry is coupled to receive electrode signals from at least one intrathoracic electrode and configured to produce intrathoracic electrogram (EGM) waveform data, and wherein the stress test data set comprises the intrathoracic electrogram (EGM) waveform data.

34. The implantable medical device (IMD) as recited in claim 32, wherein the electrode sensing circuitry is coupled to receive electrode signals from at least one intracardiac electrode and configured to produce intracardiac electrogram (EGM) waveform data, and wherein the stress test data set comprises the intracardiac electrogram (EGM) waveform data.

35. The implantable medical device (IMD) as recited in claim 32, wherein the electrogram (EGM) waveform comprises an ST segment and an isoelectric baseline, and wherein the electrogram (EGM) waveform data comprises data indicative of a deviation of the ST segment from the isoelectric baseline.

36. The implantable medical device (IMD) as recited in claim 22, wherein the control unit is coupled to receive sensor data, and wherein the stress test data set comprises the sensor data.

37. The implantable medical device (IMD) as recited in claim 22, wherein the control unit is coupled to receive pacing threshold data produced within the IMD and indicative of an amount of energy dissipated by the pacing circuitry while producing the pacing pulses, and wherein the stress test data set comprises the pacing threshold data.

38. The implantable medical device (IMD) as recited in claim 22, wherein the control unit is coupled to receive arrhythmia data produced within the IMD and indicative of detected arrhythmias of the heart of the patient, and wherein the stress test data set comprises the arrhythmia data.

39. The implantable medical device (IMD) as recited in claim 22, further comprising timing/pacing control circuitry coupled to receive a first intrinsic depolarization signal and a second intrinsic depolarization signal from the heart of the patient, wherein the IMD is programmable to operate in a demand mode, and wherein in the demand mode, if the timing/pacing control circuitry does not receive the second intrinsic depolarization signal within a predetermined time period, determined by the pacing rate, after the timing/pacing control circuitry receives the first intrinsic depolarization signal, the timing/pacing control circuitry is configured to signal the pacing circuitry to produce one of the pacing pulses.

40. The implantable medical device (IMD) as recited in claim 22, further comprising a telemetry unit coupled to the control unit and configured to send and receive signals and data, wherein during an initial portion of the first stress test protocol, the control unit: (i) programs the pacing rate such that the pacing rate is increased from the start rate to the stop rate, and (ii) acquires and stores the stress test data in the memory, and wherein during a final portion of the first stress test protocol, the control unit: (iii) programs the pacing rate such that the pacing rate is decreased from the stop rate to the start rate, and (iv) provides the stress test data set stored in the memory via the telemetry unit.

41. A medium for producing control signals for executing an instruction set in an implantable medical device (IMD) to perform a method of detecting a symptomatic or asymptomatic episode of myocardial ischemia, said medium comprising:

(i) instructions for performing a first stress test protocol wherein a programmable pacing rate is slowly increased at from between about five paces per minute (ppm) to about ten ppm from a start rate to a stop rate, wherein the stop rate is greater than the start rate, and including instructions for acquiring and storing a patient's response to the first stress test protocol in a memory structure as a part of a stress test data set;

(ii) instructions for performing a second stress test protocol according to stored timing information specifying a time the IMD is to subject the patient to the first stress test protocol, and including instructions to subject the patient to the first stress test protocol at the time, day and/or date specified by the timing information, and including instructions for acquiring and storing the patient's response to the second stress test protocol in the memory structure as a part of the stress test data set; and (iii) instructions for performing a third stress test protocol wherein the protocol comprises recreating the physiologic conditions of a previously stored episode of paced or intrinsic symptomatic myocardial ischemia that were stored in the memory structure after the patient triggers an episode storage event, and including acquiring and storing the patient's response to the third stress test protocol in the memory structure as a part of the stress test data set.

* * * * *